United States Patent [19]
Batchelor et al.

[11] Patent Number: 6,133,257
[45] Date of Patent: Oct. 17, 2000

[54] FUSED POLYCYCLIC 2-AMINOPYRIMIDINE DERIVATIVES

[75] Inventors: Mark James Batchelor, Cumnor Hill; Jeremy Martin Davis, Wokingham; David Festus Charles Moffat, Maidenhead; Peter David Davis, Aston Rowant, all of United Kingdom

[73] Assignee: Celltech Therapeutics Limited, United Kingdom

[21] Appl. No.: 09/099,171

[22] Filed: Jun. 18, 1998

[30] Foreign Application Priority Data

Jun. 20, 1997 [GB] United Kingdom .................. 9713087

[51] Int. Cl.$^7$ ...................... A61K 31/517; C07D 239/70; C07D 403/12
[52] U.S. Cl. ................. 514/218; 514/232.8; 514/252.16; 514/267; 544/115; 544/249; 540/575
[58] Field of Search ..................................... 544/279, 115, 544/249; 514/267, 253, 218, 232.8, 252.16; 540/575

[56] References Cited

U.S. PATENT DOCUMENTS

| | | | |
|---|---|---|---|
| 3,947,467 | 3/1976 | Verge et al. ........................ | 260/310 R |
| 4,012,495 | 3/1977 | Schmiechen et al. .................. | 514/424 |
| 4,015,017 | 3/1977 | Gazave .................................... | 514/687 |

(List continued on next page.)

FOREIGN PATENT DOCUMENTS

| | | |
|---|---|---|
| 0 031 104 A1 | 7/1981 | European Pat. Off. . |
| 0 048 763 A1 | 4/1982 | European Pat. Off. . |
| 0 233 461 A2 | 8/1987 | European Pat. Off. . |
| 0 295 210 A1 | 12/1988 | European Pat. Off. . |
| 0 337 943 A2 | 10/1989 | European Pat. Off. . |
| 0 393 500 A1 | 10/1990 | European Pat. Off. . |
| 0 490 823 A1 | 6/1991 | European Pat. Off. . |
| 0 470 805 A1 | 2/1992 | European Pat. Off. . |
| 0 497 564 A1 | 8/1992 | European Pat. Off. . |
| 0 511 865 A1 | 11/1992 | European Pat. Off. . |
| 0 537 742 A2 | 4/1993 | European Pat. Off. . |
| 0 564 409 A1 | 10/1993 | European Pat. Off. . |
| 1 285 932 | 8/1972 | France . |
| 2 313 422 | 12/1976 | France . |
| 2 545 356 A1 | 11/1984 | France . |
| 250 1443 | 7/1975 | Germany . |
| 3-77872 | 4/1991 | Japan . |
| 3-77923 | 4/1991 | Japan . |
| 1588639 | 4/1981 | United Kingdom . |

(List continued on next page.)

OTHER PUBLICATIONS

Kroon, A.P. et al., "SN(ANRORC) [addition nucleophilic ring opening–ring closing]–mechanism. XIII. SN(AN-RORC) mechanism in the amination of 2–substituted 4–phenylpyrimidines with potassijm amide in liquid ammonia," Recl. Trav. Chim. Pays–Bas, 1974, 93(12), 325–328, Chemical Abstract No. 83:43256.

Ife, R.J., "Aminopyrimidinone derivaties as histamine H1–antagonists", CAPLUS Abstract No. 101:211163, Registry No. 92993–05–0, Jul. 4, 1984, 2 pages.

Ashton, "Selective Type IV Phosphodiesterase Inhibitors as Antiasthmatic Agents. The Syntheses and Biological Activities of 3–(Cyclopentyloxy)–4–methyoxybenzamides and Analogues", J. Med. Chem., 1994, 37, 1696–1703.

Beavo & Reifsnyder, "Primary Sequence of Cyclic Nucleotide Phosphodiesterase Isozymes and the Design of Selective Inhibitors" TIPS, 1990, 11, 150–155.

Buu–Hoi, N.P. et al., "Bromination of Some 1,2,2–Triarylethylenes" J. of Organic Chemistry, 1958, 1261–1263.

Buu–Hoi et al., "New Method for the Synthesis of ω,ω–Diarylacetophenones Aminated in the Aromatic Nucleus. Plynitration of Triarylethylenes", Chem. Abstr., 1964, 61(13), 16006h.

(List continued on next page.)

Primary Examiner—Richard L. Raymond
Attorney, Agent, or Firm—Woodcock Washburn Kurtz Mackiewicz & Norris LLP

[57] ABSTRACT

Fused polycyclic 2-aminopyrimidines of formula (1) are described:

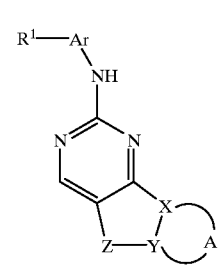

(1)

wherein
$R^1$ is a group —$L^1 R^2$ where $L^1$ is a covalent bond or a linker atom or group and $R^2$ is a group —$(Alk)_m L^2 R^3$ where Alk is an optionally substituted aliphatic or heteroaliphatic chain, m is zero or the integer 1, $L^2$ is a covalent bond or a linker atom or group and $R^3$ is an optionally substituted cycloaliphatic or heterocycloaliphatic group provided that when m is zero
$L^2$ is a covalent bond;
Ar is an aryl or heteroaryl group;
X is a carbon or nitrogen atom;
Y is a carbon or nitrogen atom;
Z is a linker group;
A together with X and Y forms an optionally substituted monocyclic or bicyclic aromatic or heteroaromatic group;
and the salts, solvates, hydrates and N-oxides thereof.
The compounds are potent and selective inhibitors of protein kinases, especially src-family protein kinases and are of use in the prophylaxis and treatment of immune diseases, hyperproliferative disorders and other diseases in which inappropriate protein kinase action is believed to have a role.

9 Claims, No Drawings

U.S. PATENT DOCUMENTS

| | | | |
|---|---|---|---|
| 4,153,713 | 5/1979 | Huth et al. | 514/423 |
| 4,193,926 | 3/1980 | Schmiechen et al. | 548/517 |
| 4,303,649 | 12/1981 | Jones | 514/8 |
| 4,548,940 | 10/1985 | Ife | 514/272 |
| 4,694,009 | 9/1987 | Hubele et al. | 514/269 |
| 4,788,195 | 11/1988 | Torley et al. | 514/252 |
| 4,792,561 | 12/1988 | Walker et al. | 514/312 |
| 4,876,252 | 10/1989 | Torley et al. | 514/224.8 |
| 4,897,396 | 1/1990 | Hubele | 514/275 |
| 4,921,862 | 5/1990 | Walker et al. | 514/312 |
| 4,966,622 | 10/1990 | Rempfler et al. | 71/92 |
| 4,971,959 | 11/1990 | Hawkins | 514/150 |
| 4,987,132 | 1/1991 | Mase et al. | 514/252 |
| 5,124,455 | 6/1992 | Lombardo | 546/181 |
| 5,128,358 | 7/1992 | Saccomano et al. | 514/392 |
| 5,159,078 | 10/1992 | Rempfler et al. | 544/330 |
| 5,164,372 | 11/1992 | Matsuo et al. | 514/19 |
| 5,175,167 | 12/1992 | Zipperer et al. | 514/277 |
| 5,177,085 | 1/1993 | Naef | 514/307 |
| 5,236,918 | 8/1993 | Amschler et al. | 514/247 |
| 5,274,002 | 12/1993 | Hawkins | 514/530 |
| 5,298,511 | 3/1994 | Waterson | 514/311 |
| 5,326,898 | 7/1994 | Chandraratna | 560/17 |
| 5,340,827 | 8/1994 | Beeley et al. | 514/352 |
| 5,491,147 | 2/1996 | Boyd et al. | 514/247 |
| 5,521,184 | 5/1996 | Zimmermann | 514/252 |
| 5,550,137 | 8/1996 | Beeley et al. | 514/354 |
| 5,580,888 | 12/1996 | Warrellow et al. | 514/332 |
| 5,593,997 | 1/1997 | Dow et al. | 514/258 |
| 5,608,070 | 3/1997 | Alexander et al. | 546/270 |
| 5,622,977 | 4/1997 | Warrellow et al. | 514/336 |
| 5,633,257 | 5/1997 | Warrellow et al. | 514/277 |
| 5,674,880 | 10/1997 | Boyd et al. | 514/307 |
| 5,691,376 | 11/1997 | Caggiano et al. | 514/532 |
| 5,693,659 | 12/1997 | Head et al. | 514/357 |
| 5,698,711 | 12/1997 | Palfreyman | 549/66 |
| 5,716,967 | 2/1998 | Kleinman | 514/313 |
| 5,723,460 | 3/1998 | Warrellow et al. | 514/247 |
| 5,728,708 | 3/1998 | Zimmermann | 514/275 |
| 5,739,144 | 4/1998 | Warrellow et al. | 514/277 |
| 5,753,663 | 5/1998 | Flippin et al. | 514/257 |
| 5,776,958 | 7/1998 | Warrellow et al. | 514/345 |
| 5,780,477 | 7/1998 | Head et al. | 514/277 |
| 5,780,478 | 7/1998 | Alexander et al. | 514/277 |
| 5,786,354 | 7/1998 | Warrellow et al. | 514/277 |
| 5,798,373 | 8/1998 | Warrellow | 514/357 |
| 5,849,770 | 12/1998 | Head et al. | 514/357 |
| 5,851,784 | 12/1998 | Owens et al. | 435/19 |
| 5,859,034 | 1/1999 | Warrellow et al. | 514/357 |
| 5,866,593 | 2/1999 | Warrellow et al. | 514/336 |
| 5,891,896 | 4/1999 | Warrellow et al. | 514/357 |
| 5,922,741 | 7/1999 | Davis et al. | 514/341 |

FOREIGN PATENT DOCUMENTS

| | | |
|---|---|---|
| WO 86/02353 | 4/1986 | WIPO . |
| WO 87/06576 | 11/1987 | WIPO . |
| WO 91/15451 | 10/1991 | WIPO . |
| WO 91/16892 | 11/1991 | WIPO . |
| WO 92/00968 | 1/1992 | WIPO . |
| WO 92/06085 | 4/1992 | WIPO . |
| WO 92/06963 | 4/1992 | WIPO . |
| WO 92/07567 | 5/1992 | WIPO . |
| WO 92/12961 | 8/1992 | WIPO . |
| WO 92/19594 | 11/1992 | WIPO . |
| WO 92/19602 | 11/1992 | WIPO . |
| WO 93/10118 | 5/1993 | WIPO . |
| WO 93/19748 | 10/1993 | WIPO . |
| WO 94/02465 | 2/1994 | WIPO . |
| WO 94/10118 | 5/1994 | WIPO . |
| WO 94/12461 | 6/1994 | WIPO . |
| WO 94/13661 | 6/1994 | WIPO . |
| WO 94/14742 | 7/1994 | WIPO . |
| WO 94/15954 | 7/1994 | WIPO . |
| WO 94/15955 | 7/1994 | WIPO . |
| WO 94/20446 | 9/1994 | WIPO . |
| WO 94/20455 | 9/1994 | WIPO . |
| WO 95/04046 | 2/1995 | WIPO . |
| WO 95/09847 | 4/1995 | WIPO . |
| WO 95/09851 | 4/1995 | WIPO . |
| WO 95/09852 | 4/1995 | WIPO . |
| WO 95/09853 | 4/1995 | WIPO . |
| WO 95/13811 | 5/1995 | WIPO . |
| WO 95/15973 | 6/1995 | WIPO . |
| WO 95/17386 | 6/1995 | WIPO . |
| WO 95/31451 | 11/1995 | WIPO . |
| WO 95/33727 | 12/1995 | WIPO . |
| WO 95/35281 | 12/1995 | WIPO . |
| WO 95/35283 | 12/1995 | WIPO . |
| WO 95/35314 | 12/1995 | WIPO . |
| WO 96/01644 | 1/1996 | WIPO . |
| WO 96/14843 | 5/1996 | WIPO . |
| WO 96/22966 | 8/1996 | WIPO . |
| WO 97/03094 | 1/1997 | WIPO . |
| WO 97/09297 | 3/1997 | WIPO . |
| WO 97/09325 | 3/1997 | WIPO . |
| WO 97/04247 | 2/1998 | WIPO . |
| WO 98/04913 | 2/1998 | WIPO . |
| 98/28281 | 7/1998 | WIPO . |
| 98/58926 | 12/1998 | WIPO . |

OTHER PUBLICATIONS

Bortolus et al., "cis–trans Isomerization of azastilbenes photosensitized by biacetyl", *Mol. Photochem.,* 1970, 2(4), 311–321, CAPLUS accession No. 1971–434722, 2 pages.

Chan, A.C. et al., "The Role of Protein Tyrosine Kinases and Protein Tyrosine Phosphatases in T Cell Antigen Receptor Signal Transduction", *Annu. Rev. Immunol.,* 1994, 12, 555–592.

Chatterjee, A. et al., "Total Synthesis of Ring–C Aromatic 18–Nor Steroid", *Tetrahedron,* 1980, 36, 2513–2519.

Chemical Abstracts, "Hypoglycemic Pharmaceuticals Containing Manzammide Derivatives", *Chem. Abstr.,* 1983, 99(6), No. 43558Z.

Chemical Abstracts. Registry Handbook—Number Section. Printed Issues Columbus US *compounds with registry nos. 95992–21–5 (CARHBT(RN1) 1RN–1648RN(1985); 95971–60–1 (CARHBT(RN1) 1RN–1648RN(1985); 90053–37–5 (CARHBT(RM1) 1RM–1426RM(1984); 82668–18–6 (CARHBT(RK2) 1515RK–2955RK(1 982); 80395–25–1 (CARHBT(RK1) 1RK–1514RK(1982); 49610–49–3 (CARHBT(RC1) 1RC–1650RC(1974).

Chemical Abstracts, Registry No. 2732–15–2, prior to 1967, 1 page.

Chemical Abstracts, Registry No. 4593–13–9, prior to 1967, 1 page.

Clayton, S.E. et al., "Direct Aromatic tert–Butylation during the Synthesis of Thiochroman–4–ones", *Tetrahedron,* 1993, 49(4), 939–946.

Collins, R.F. et al., "The Chemotherapy of Schistosomiasis. Part IV. Some Ethers of 4–Amino–2–methoxyphenol", *J. Chem. Soc.,* 1961, 1863–1879.

Daves, G.D. et al., "Pyrimidines. XIII. 2– and 6–Substituted 4–Pyrimidinecarboxylic Acids", *J. Of Hev. Chem.,* 1964, 1, 130–133.

Degani, I. et al., "Cationi etero–aromatici Nota VI—Sintesi di alcuni derivati del perclorato di tiacromilio", *Boll. Sci. Fac. Chim. Ind. Bologna,* 1966, 24(2–3), 75–91 (English Summary Only).

Dietl, F. et al., "Chinone von Benzo–und Dibenzokronenethern", *Synthesis,* 1985, 626–631.

Dent et al., "Inhibition of eosinophil cyclic nucleotide PDE activity and opsonised zymosan–stimulated respiratory burst by 'type IV'–selective PDE inhibitors", *Br. J. Pharmacol.,* 1991, 103, 1339–1346.

El–Wakil et al., "Study of the proton magnetic resonance of methoxytamoxifen towards ortho–substitiution", *Chem. Abstr.,* 1992, 116, 255248t.

Geissler, J.F. et al., "Thiazolidine–Diones. Biochemical and Biological Activity of a Novel Class of Tyrosine Protein Kinase Inhibitors", *J. Of Biol. Chem.,* 1990, 265(36), 22255–22261.

Griffin, R.W. et al., "1–Methyl–7–halo–2–naphthalenecarboxylic Acid Derivatives", *J. Organic Chem.,* 1964, 29(8), 2109–2116.

Gupta, A.S. et al., "Friedel–Crafts Condensation of Ethyl Allylmalonate with Anisole", *Tetrahedron,* 1967, 23, 2481–2490.

Hanks, S.K. et al., "The eukaryotic protein kinase superfamily: kinase (catalytic) domain structure and classification", *FASEB J.,* 1995, 9, 576–596.

Hart et al., "Alkylation of Phenol with a Homoallylic Halide", *J. Am. Chem. Soc.,* 1963, 85, 3269–3273.

Heaslip et al., "Phosphodiesterase–IV Inhibition, Respiratory Muscle Relaxation and Bronchodilation by WAY–PDA–641", *J. Pharm. Exper. Ther.,* 1993, 268(2), 888–896.

Hirose et al., "Styrene Derivatives and Electrophotpgraphic Photoreceptor Containing Them", *Chem. Abstr.,* 1993, 118, 136183z.

Ishikura, M. et al., "An Efficient Synthesis of 3–Heteroarylpyridines via Diethyl–(3–pyridyl)–borane" *Synthesis,* 1984, 936–938.

Iwashita, S. et al., "Signal Transduction System for Growth Factor Receptors Associated with Tyrosine Kinase Activity: Epidermal Growth Factor Receptor Singalling and Its Regulation", *Cellular Signalling,* 1992, 4(2), 123–132.

Johnson et al., "Identification of Retinoic Acid Receptor β Subtype Specific Agonists", *J. Med. Chem.,* 1996, 39(26), 5027–5030.

Kaiser et al., "Selective metalations of methylated pyridines and quinolines", *J. Org. Chem.,* 1973, 38(1), 71–75, CAPLUS accession No. 1973–71853, 2 pages.

Karlsson et al., "T–Lymphocyte and Inflammatory Cell Research in Asthma", Joller, G. et al. (eds.), Academic Press, 1993, 323–347.

Kefalas, P. et al., "Signalling by the p60$^{c-src}$ Family of Protein–Tyrosine Kinases", *Int. J. Biochem. Cell Biol.,* 1995, 27(6), 551–563.

Lehmann, J. et al., "Lactones; XIII. Grignard Reaction Followed by Phase–Transfer Oxidation: A Convenient Synthesis of γ,γ–Distributed γ–Butyrolactones from γ–Butyrolactone", *Synthesis,* 1987, 1064–1067 (English abstract only).

Lisle, H. et al., "IL–2–Induced Eosinophilia in the Rat Pleural Cavity: The Effect of Dexamethasone and Indomethacin", *Br. J. Pharmacol.* 1993, 108, 230.

Livi et al., "Cloning and Expression of cDNA for a Human Low–$K_m$3 Rolipram–sensitive Cyclic AMP Phosphodiesterase", *Molecular and Cellular Biol.* 1990, 10(6), 2678–2686.

Manhas et al., "Heterocyclic Compounds XII. Quinazoline Derivatives as Potential Antifertility Agents(1)" *J. Heterocyclic Chem.,* 1979, 16, 711–715.

Mathison et al., "Synthesis and Hypotensive Properties of Tetrahydroixoquinolines", *J. Med. Chem.,* 1973, 16(4), 332–336.

Meyers, A.J. et al., "Oxazolines. XI. Synthesis of Functionalized Aromatic and Aliphatic Acids. A Useful Protecting Group for Carboxylic Acids Against Grignard and Hydride Reagents", *J. Org. Chem.* 1974, 39(18), 2787–2793.

Meyers, A.I. et al., "The Synthesis of 2–Pyridones from Cyclic Cyano Ketones. A New Aromatization Procedure for Dihydro–2–pyridones", *J. Org. Chem.,* 1964, 29, 1435–1438.

Mezheritskaya, "Synthesis and properties of carboxonium het=erocyclic systems. VII. Synthesis and properties of 2–benzyl–substituted 1,3–dioxolanium salts", *Chem. Abstr.,* 1980, 93, 95160j, 635.

Mitsunobu, O., "The Use of Diethyl Azodicarboxylate and Triphenylphosphine in Synthesis and Transformation of Natural Products" *Synthesis,* 1981, 1–28.

Miyaura, N. et al., "The Palladium–Catalyzed Cross–Coupling Reaction of Phenylboronic Acid with Haloarenes in the Presence of Bases", *Synth. Comm.,* 1981, 11, 513–519.

Newton, A.C., "Protein Kinase C: Structure, Function, Regulation", *J. Biol. Chem.,* 1995, 270(48), 28495–28498.

Nicholson et al., "Differential Modulation of Tissue Function and Therapeutic Potential of Selective Inhibitors of Cyclic Nucleotide Phosphodiesterase Isoenzymes" *TIPS,* 1991, 12, 19–27.

O'Connor et al., "Voltammetry and Controlled Potential Oxidation of 3,4–dimethoxypropenylbenzene at a rotating platinum electrode in unbuffered acetonitrile and in acetonitrile–pyridine solution" *Chem. Abstr.,* 1964, 60(8) #10203.4.

Ohtani, Y. et al., "Studies on Pitch Problems Caused by Pulping and Bleaching of Tropical Woods. XIV. Chemistry of the Aurone Derivatives at the Conventional Bleaching Stages", *Acta Chem. Scand.,* 1982, 613–621.

Pickett, W.C. et al., "Modulation of Eicosanoid Biosynthesis by Novel Pyridinylpyrimidines", *Ann. N.Y. Acad. Sci.,* 1994, 744, 299–305.

Pines, J., "Cyclins and cyclin–dependent kinases: take your partners", *TIBS,* 1993, 18, 195–197.

Plé, N. et al., "Metalation of Diazines. XI. Directed Ortho–Lithiation of Fluoropyrimidines and Application to Synthesis of an Azacarboline", *J. Heterocyclic Chem.,* 1994, 31, 1311–1315.

Porter et al., "Preparation of 6–phenyl–3–(5–tetrazolyl)pyridin–=2(H)–one Derivatives as Cyclic AMP–dependent Protein Kinase Agonists" *Chem. Abstr.,* 1992, 117(9), 90296n.

Ramalingam, Deshmukh and Sattur, "Synthesis and Pharmacology of 2,5–Disubstituted 1,3,4–Zxadiazoles" *J. Indian Chem. Soc.,* 1981, 58(3), 269–271.

Reddy et al., "Inhibition of Breast Cancer Cell Growth in Vitro by a Tyrosine Kinase Inhibitor" *Cancer Research,* 1992, 52, 3636–3641.

Sakakibara, K. et al., "Preparation of N–pyridyl–4–(benzyloxy)benzamides as Cardiotonics", *Chem. Abstr.,* 1988, 108, No. 131583p.

Sánchez, H.I. et al., "Formal Total Syntehsis of β–Pipitzol", *Tetrahedron,* 1985, 41(12), 2355–2359.

Schneider et al., "Catechol Estrogens of the 1,1, 2–Triphenylbut–1–ene Type: Relationship Between Structure, Estradiol Receptor Affinity, Estrogenic and Antiestrogenic Properties, and Mammary Tumor Inhibiting Activities" *J. Med. Chem.,* 1986, 29, 1355–1362.

Seitz et al., "Fluorotamoxifen. A Caveat on the Generality of Electrophilic Destannylation" *Chem. Abstr.,* 1989, 111, 57133k.

Sharp, M.J. et al., "Synthetic Connections to the Aromatic Directed Metalation Reaction. Functionalized Aryl Boronic Acids by Ipso Borodesilylation; General Synthesis of Unsymmetrical iphenyls and n–Terphenyls", *Tetrahedron Lett.,* 1987, 28(43), 5093–5096.

Shioiri et al., "New Methods and Reagents in Organic Synthesis. 3. Diethyl Phosphorocyanidate: A New Reagent for C–Acylation", *J. Org. Chem.,* 1978, 43, 3631–3632.

Spada, A.P. et al., "Small Molecule Inhibitors of Tyrosine Kinase Activity", *Exp. Opin. Ther. Patents,* 1995, 5(8), 805–817.

Takeuchi, I. et al., "On the Antimocrobial Activity and Syntheses of Carbanilide and Salicylanilide Derivatives", *Chem. Abstr.,* 1983, 98, No. 125577y.

Thompson, W.J. and Gaudino, J., "A General Synthesis of 5–Arylnicotinates" *J. Org. Chem.,* 1984, 49, 5237–5243.

Tominaga et al., "Polarized Ethylenes. IV. Synthesis of Polarized Ethylenes Using Thioamides and Methyl Dithiocarboxylates and Their Application to Syntheses of Pyrazoles, Pyrimidines, Pyrazolo[3,4–d]pyrimidines, and 5–Aza [2.2.3]cyclazines", *J. Het. Chem.,* 1990, 27, 647–660.

Trost and Fleming (eds.), *Comprehensive Organic Synthesis,* Pergamon Press, New York, 1991, 3, 531–541.

Tsutsumi, K. et al., "Preparation of (Dialkoxyphosphinoylmethyl) benzamides as Antihyperlipidemics", *Chem. Abstr.,* 1990, 113, No. 6599a.

Vidal et al., "Electrophilic Amination: Preparation and Use of N–Boc–3–(4–cyanophenyl)oxaziridine, a New Reagent That Transfers a N–Boc Group to N– and C–Nucleophiles", *J. Org. Chem.,* 1993, 58, 4791–4793.

Yamaguchi, H., "Guanidinobenzene derivatives as anticoagulants", *Chem. Absts.,* 1989, 110, 655 (Abstract No. 94706z).

Yeadon et al., "Mechanisms Contributing to Ozone–Induced Bronchial Hyperreactivity in Guinea Pigs", *Pulmonary Pharm.,* 1992, 5, 39–50.

Yoneda et al., "The Antiproliferative Effects of Tyrosine Kinase Inhibitors Tyrphostins on a Human Squamous Cell Carcinoma in Vitro and in Nude Mice" *Cancer Research,* 1991, 51, 4430–4435.

Zimmermann, J. et al., "Phenylamino–Pyrimidine (PAP) Derivatives: A New Class of Potent and Selective Inhibitors of Protein Kinase C (PKC)", *Arch. Pharm.,* 1996, 329(7), 371–376.

Zimmermann, J. et al, "Phenylamino–Pyrimidine (PAP)—Derivatives: A New Class of Potent and Highly Selective PDGF–Receptor Autophosphorylation Inhibitors", *Bioorg. Med. Chem. Lett.,* 1996, 6(11), 1221–1226.

Zimmermann, J. et al., "Potent and Selective Inhibitors of the ABL–Kinase Phenylamino–Pyrimidine (PAP) Derivatives", *Bioorg. Med. Chem. Lett.,* 1997, 7(2), 187–192.

Ames, D.E. et al., "Some Dipyridylalkanes", *J. Chem. Soc.,* 1962, 1475–1481.

Barton, D. et al., "A useful synthesis of pyrroles from nitroolefins", *Tetrahedron,* 1990, 46(21), 7587–7598 (HCAPLUS 1991:163917, 2 pages).

Fitzgerald, J.J. et al., "Reaction of benzocyclobutene oxides with nitriles: synthesis of hypercumine and other 3–substituted isoquinolines", *Tetrahedron Lett.,* 1994, 35(49), 9191–9194 (HCAPLUS 1995:272292, 2 pages).

Hanna, M.M. et al., "Syntheis and antimicrobial activity of some substituted 3–aryl–5–benzylidene–2–phenyl–4–imidazolone derivatives", *Bull. Fac. Pharm.,* 1994, 32(3), 353–359 (HCAPLUS 1996:586501, 2 pages).

Nanjo et al., "Preparation of 2–anilinopyrimidines as agricultural fungicides", *Chem. Abstr.,* 1992, 116(21), No. 116:209703q.

Tollari, S. et al., "Intramolecular amination of olefins. Synthesis of 2–substituted–4–quinolones from 2–nitrochalcones catalyzed by ruthenium", *J. Chem. Soc.,* 1994, 15, 1741–1742 (HCAPLUS 1994:605194, 2 pages).

Yamato, M. et al., "Chemical structure and sweet taste of isocoumarin and related compounds. VI", *Chem. Pharm. Bull.,* 1975, 23(12), 3101–3105 (HCAPLUS 1976:99154, 2 pages).

Abraham, W.M. et al., "$\alpha_4$–Integrins Mediate Antigen–Induced Late Bronchial Responses and Prolonged Airway Hyperresponsiveness in Sheep", *J. Clin. Invest.,* 1994, 93, 776–787.

Berlin, C. et al., "$\alpha 4\beta 7$ Integrin Mediates Lymphocyte Binding to the Mucosal Vascular Addressin MAdCAM–1", *Cell,* 1993, 74, 185–195.

Binns, R.M. et al., "The Role of E–Selectin in Lymphocyte and Polymorphonuclear Cell Recruitment into Cutaneous Delayed Hypersensitivity Reactions in Sensitized Pigs", *J. Immunol.,* 1996, 157, 4094–4099.

Briskin, M.J. et al., "Structural Requirements for Mucosal Vascular Addressin Binding to Its Lymphocyte Receptor $\alpha_4\beta_7$", *J. Immunol.,* 1996, 156, 719–726.

Cardarelli, P.M. et al., "Cyclic RGD Peptide Inhibits $\alpha 4\beta 7$ Interaction with Connecting Segment 1 and Vascular Cell Adhesion Molecule", *J. Biol. Chem.,* 1994, 269(28), 18668–18673.

Ferguson, T.A. et al., "Two integrin–binding peptides abrogate T cell–mediated immune responses in vivo", *Proc. Natl. Acad. Sci. USA,* 1991, 88, 8072–8076.

Holzmann, B. et al., "Peyer's patch–specific lymphocyte homing receptors consist of a VLA–4–like $\alpha$ chain associated with either of two integrin $\beta$ chains, one of which is novel", *EMBO J.,* 1989, 8(6), 1735–1741.

Humphries, M.J. et al., "Mechanisms of VCAM–1 and fibronectin binding to integrin $\alpha_4\beta_1$: implications for integrin function and rational drug design", *Ciba Foundation Symposium,* 1995, 189, 177–194.

Issekutz, T.B., "Inhibition of Lymphocyte Endothelial Adhesion and In Vivo Lymphocyte Migration to Cutaneous Inflammation by TA–3, a New Monoclonal Antibody to Rat LFA–1", *J. Immunol.,* 1992, 149(10), 3394–3402.

Li, Z. et al., "Effect of an anti–Mo1 MAb on ozone–induced airway inflammation and airway hyperresponsiveness in dogs", *Am. J. Physiol.,* 1992, 263(6 Pt 1), L723–726.

Marlin, S.D. et al., "LFA–1 Immunodeficiency Disease", *J. Exp. Med.,* 1986, 164, 855–867.

Osborn, L. et al., "Direct Expression Cloning of Vascular Cell Adhesion Molecule 1, a Cytokine–Induced Endothelial Protein that Binds to Lymphocytes", *Cell,* 1989, 59, 1203–1211.

Podolsky, D.K. et al., "Attenuation of Colitis in the Cotton–top Tamarin by Anti–$\alpha 4$ integrin Monoclonal Antibody", *J. Clin. Invest.,* 1993, 92, 372–380.

Shroff, H.N. et al., "Small Peptide Inhibitors of $\alpha_4\beta_7$ Mediated MAdCAM–1 Adhesion to Lymphocytes", *Barge. Med. Chem. Letts.,* 1996, 6(21), 2495–2500.

Sonnenberg, A., "Integrins and Their Ligands", *Curr. Topics Microbiol. Immunol.,* 1993, 184, 7–35.

Springer, T.A., "Adhesion receptors of the immune system", *Nature,* 1990, 346, 425–434.

Springer, T.A., "Traffic Signals for Lymphocyte Recirculation and Leukocyte Emigration: The Multistep Paradigm", *Cell,* 1994, 76, 301–314.

Vanderslice, P. et al., "A Cyclic Hexapeptide is a Potent Antagonist of α4 Integrins", *J. Immunol.,* 1997, 158, 1710–1718.

Yang, X., "A predominant role of integrin α4 in the spontaneous development of autoimmune diabetes in nonobese diabetic mice", *Proc. Natl. Acad. Sci. USA,* 1994, 91, 12604–12608.

Yednock, T.A., "Prevention of experimental autoimmune encephalomyelitis by antibodies against α4β1 integrin", *Nature,* 1992, 356, 63–66.

FUSED POLYCYCLIC 2-AMINOPYRIMIDINE DERIVATIVES

This invention relates to a series of fused polycyclic 2-aminopyrimidines, to processes for their preparation, to pharmaceutical compositions containing them, and to their use in medicine.

Protein kinases participate in the signalling events which control the activation, growth and differentiation of cells in response to extracellular mediators and to changes in the environment. In general, these kinases fall into two groups; those which preferentially phosphorylate serine and/or threonine residues and those which preferentially phosphorylate tyrosine residues [Hanks, S K, Hunter T, FASEB. J. 9, 576–596 (1995)]. The serine/threonine kinases include for example, protein kinase C isoforms [Newton A C, J. Biol. Chem. 270, 28495–28498 (1995)] and a group of cyclin-dependent kinases such as cdc2 [Pines J, Trends in Biochemical Sciences 18, 195–197 (1995)]. The tyrosine kinases include membrane-spanning growth factor receptors such as the epidermal growth factor receptor [Iwashita S and Kobayashi M. Cellular Signalling 4, 123–132 (1992)], and cytosolic non-receptor kinases such as ZAP-70 and csk kinases [Chan C et al Ann. Rev. Immunol. 12, 555–592 (1994)]. A particular group of non-receptor tyrosine kinases are a group known as the src family which includes p56$^{lck}$ and p59$^{fyn}$ [Kefelas P et al International Journal of Biochemistry and Cell Biology 27, 551–563 (1995)].

Inappropriately high protein kinase activity has been implicated in many diseases resulting from abnormal cellular function. This might arise either directly or indirectly, for example by failure of the proper control mechanisms for the kinase, related for example to mutation, overexpression or inappropriate activation of the enzyme; or by over- or underproduction of cytokines or growth factors also participating in the transduction of signal upstream or downstream of the kinase. In all of these instances, selective inhibition of the action of the kinase might be expected to have a beneficial effect.

We have now found a series of fused polycyclic 2-aminopyrimidine derivatives which are potent and selective inhibitors of protein kinases, especially src-family protein kinases. The compounds are thus of use in the prophylaxis and treatment of immune diseases, hyperproliferative disorders and other diseases in which inappropriate protein kinase action is believed to have a role.

Thus according to one aspect of the invention, we provide a compound of formula (1):

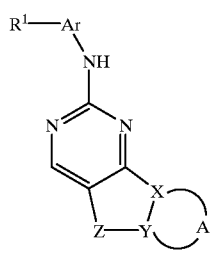

(1)

wherein
$R^1$ is a group —$L^1R^2$ where $L^1$ is a covalent bond or a linker atom or group and $R^2$ is a group -(Alk)$_m$L$^2$R$^3$ where Alk is an optionally substituted aliphatic or heteroaliphatic chain, m is zero or the integer 1, $L^2$ is a covalent bond or a linker atom or group and $R^3$ is an optionally substituted cycloaliphatic or heterocycloaliphatic group provided that when m is zero $L^2$ is a covalent bond;
Ar is an aryl or heteroaryl group;
X is a carbon or nitrogen atom;
Y is a carbon or nitrogen atom;
Z is a linker group;
A together with X and Y forms an optionally substituted monocyclic or bicyclic aromatic or heteroaromatic group;
and the salts, solvates, hydrates and N-oxides thereof.

When in the compounds of formula (1) $L^1$ and/or $L^2$ is present as a linker atom or group each may be the same or different and may be for example an —O— or —S—atom or a —C(O)—, —C(S)—, —S(O)—, —S(O)$_2$—, —N(R$^4$)— [where R$^4$ is a hydrogen atom or a $C_{1-6}$ alkyl, e.g. methyl or ethyl, group], —CON(R$^4$)—, —OC(O)N (R$^4$)—, —CSN(R$^4$)—, —N(R$^4$)CO—, —N(R$^4$)C(O)O—, —N(R$^4$)CS—, —SON(R$^4$), —SO$_2$N(R$^4$), —N(R$^4$)SO$_2$—, —N(R$^4$)CON(R$^4$)—, —N(R$^4$)CSN(R$^4$)—, —N(R$^4$)SON (R$^4$)— or —N(R$^4$)SO$_2$N(R$^4$) group.

In the compounds of formula (1), when the alkylene chain represented by Alk is present it may be an optionally substituted $C_{1-10}$ aliphatic chain, for example an optionally substituted straight or branched chain $C_{1-6}$alkylene, e.g. $C_{1-3}$alkylene, $C_{2-6}$alkenylene, e.g. $C_{2-4}$alkenylene, or $C_{2-6}$alkynylene, e.g. $C_{2-4}$ alkynylene chain. Each of said chains may be optionally interrupted by one or two heteroatoms or heteroatom-containing groups represented by $L^3$ [where $L^3$ is an atom or group as just described for $L^1$], to form an optionally substituted Alk heteroaliphatic chain.

Particular examples of aliphatic chains represented by Alk include optionally substituted —CH$_2$—, —CH$_2$CH$_2$—, —(CH$_2$)$_2$CH$_2$—, —CH(CH$_3$)CH$_2$—, —(CH$_2$)$_3$CH$_2$—, —CH(CH$_3$)CH$_2$CH$_2$—, —CH$_2$CH(CH$_3$)CH$_2$—, —C(CH$_3$)$_2$ CH$_2$—(CH$_2$)$_4$CH$_2$—, —(CH$_2$)$_5$CH$_2$—, —CHCH—, —CHCHCH$_2$—, —CH$_2$CHCH$_2$—CHCH (CH$_2$)$_2$—, —CH$_2$CHCHCH$_2$—, —(CH$_2$)$_2$CHCH$_2$, —CC—, —CCCH$_2$—, —CH$_2$CC—, —CC(CH$_2$)$_2$—, —CH$_2$CCCH$_2$—, or —(CH$_2$)$_2$CC— groups. Where appropriate each of said groups may be optionally interrupted by one or two atoms and/or groups $L^3$ to form an optionally substituted heteroaliphatic chain.

The optional substituents which may be present on these aliphatic and/or heteroaliphatic chains include one, two, three or more substituents selected from halogen atoms, e.g. fluorine, chlorine, bromine or iodine atoms, or hydroxyl, $C_{1-6}$ alkoxy, e.g. methoxy or ethoxy, thiol, $C_{1-6}$ alkylthio e.g. methylthio or ethylthio, —SC(NH)NH$_2$, —CH$_2$C(NH)NH$_2$, amino or substituted amino groups.

Substituted amino groups include for example groups of formulae —NR$^5$R$^6$ where R$^5$ is an optionally substituted $C_{1-6}$ alkyl, $C_{2-6}$alkenyl or $C_{2-6}$alkynyl group optionally interrupted by one or two heteroatoms or heteroatom-containing groups represented by $L^3$ (where $L^3$ is an atom or group as described above) and $R^6$ is a hydrogen atom or is a group as just defined for $R^5$.

When $R^3$ is present in compounds of formula (1) as an optionally substituted cycloaliphatic group it may be an optionally substituted $C_{3-10}$ cycloaliphatic group. Particular examples include optionally substituted $C_{3-10}$cycloalkyl, e.g. $C_{3-7}$cycloalkyl or $C_{3-10}$cycloalkenyl e.g. $C_{3-7}$ cycloalkenyl groups.

Heterocycloaliphatic groups represented by $R^3$ include the cycloaliphatic groups just described for $R^3$ but with each group additionally containing one, two, three or four heteroatoms or heteroatom-containing groups represented by $L^4$, where $L^4$ is an atom or group as described above for $L^1$.

Particular examples of $R^3$ cycloaliphatic and heterocycloaliphatic groups include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, 2,4-cyclopentadien-1-yl, 3,5,-cyclohexadien-1-yl, pyrroline, e.g. 2- or 3-pyrrolinyl, pyrrolidinyl, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, pyranyl, e.g. 2- or 4-pyranyl, piperidinyl, 1,4-dioxanyl, morpholinyl, 1,4-dithianyl, thiomorpholinyl, piperazinyl, homopiperazinyl, 1,3,5-trithianyl, oxazinyl, e.g. 2H-1,3-, 6H-1,3-, 6H-1,2-, 2H-1,2- or 4H-1,4- oxazinyl, 1,2,5-oxathiazinyl, isoxazinyl, e.g. o- or p-isoxazinyl, oxathiazinyl, e.g. 1,2,5 or 1,2,6-oxathiazinyl, or 1,3,5,2-oxadiazinyl groups.

Optional substituents which may be present on $R^3$ cycloaliphatic and heterocycloaliphatic groups include those optional substituents described above for Alk when it is an aliphatic chain. The heterocycloaliphatic groups may be attached to the remainder of the molecule of formula (1) through any appropriate ring carbon or heteroatom.

Aryl groups represented by the group Ar in compounds of formula (1) include for example mono- or bicyclic $C_{6-12}$ optionally substituted aromatic groups, for example optionally substituted phenyl, 1- or 2-naphthyl, or indenyl groups.

Heteroaryl groups represented by Ar include for example $C_{1-9}$ optionally substituted heteroaromatic groups containing for example one, two, three or four heteroatoms selected from oxygen, sulphur or nitrogen atoms. In general, the heteroaromatic groups may be for example monocyclic or bicyclic heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example nine- to thirteen-membered heteroaromatic groups containing one, two or more heteroatoms selected from oxygen, sulphur or nitrogen atoms.

The aryl or heteroaryl groups represented by Ar may be attached to the group $R^1$ and the —NH— group of the remainder of the molecule of formula (1) through any available ring carbon or heteroatom as appropriate.

Particular examples of heteroaromatic groups represented by Ar include optionally substituted pyrrolyl, furyl, thienyl, imidazolyl, N-methylimidazolyl, N-ethyl-imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, benzotriazolyl, isobenzothienyl, indolyl, isoindolyl, benzimidazolyl, imidazo[1,2-a]pyridyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl and 5,6,7,8-tetrahydroisoquinolinyl.

Optional substituents present on the aryl or heteroaryl groups represented by Ar include one, two, three or more groups, each represented by the group $R^7$. The substituent $R^7$ may be selected from an atom or group $R^8$ or -$Alk^1$ ($R^8$)n, where $R^8$ is a halogen atom, or an amino (—$NH_2$), substituted amino, nitro, cyano, hydroxyl (—OH), substituted hydroxyl, formyl, carboxyl (—$CO_2H$), esterified carboxyl, thiol (—SH), substituted thiol, —$COR^9$ [where $R^9$ is an -$Alk^1(R^8)_n$, aryl or heteroaryl group], —$CSR^9$, —$SO_3H$, —$SO^2R^9$ —$SO_2NH_2$, —$SO_2NHR^9$, $SO_2N[R^9]_2$, —$CONH_2$, —$CSNH_2$, —$CONHR^9$, —$CSNHR^9$, —$CON[R^9]_2$, —$CSN[R^9]_2$, —$NHSO_2H$, —$NHSO_2R^9$, —$N[SO_2R^9]_2$, —$NHSO_2NH_2$, —$NHSO_2NHR^9$—$NHSO_2N[R^9]_2$, —$NHCOR^9$, —$NHCSR^9$ —$NHC(O)OR^9$, aryl or heteroaryl group; $Alk^1$ is a straight or branched $C_{1-6}$alkylene, $C_{2-6}$alkenylene or $C_{2-6}$alkynylene chain, optionally interrupted by one, two or three —O— or —S— atoms or —$S(O)_p$ [where p is an integer 1 or 2] or —$N(R^{10})$— groups [where $R^{10}$ is a hydrogen atom or $C_{1-6}$alkyl, e.g. methyl or ethyl group]; and n is zero or an integer 1, 2 or 3.

When in the group -$Alk^1(R^8)_n$ n is an integer 1, 2 or 3, it is to be understood that the substituent or substituents $R^8$ may be present on any suitable carbon atom in -$Alk^1$. Where more than one $R^8$ substituent is present these may be the same or different and may be present on the same or different atom in -$Alk^1$. Clearly, when n is zero and no substituent $R^8$ is present the alkylene, alkenylene or alkynylene chain represented by $Alk^1$ becomes an alkyl, alkenyl or alkynyl group.

When $R^8$ is a substituted amino group it may be for example a group —$NHR^9$ [where $R^9$ is as defined above) or a group —$N[R^9]_2$ wherein each $R^9$ group is the same or different.

When $R^8$ is a halogen atom it may be for example a fluorine, chlorine, bromine, or iodine atom.

When $R^8$ is a substituted hydroxyl or substituted thiol group it may be for example —$OR^9$, —$SR^9$ or —$SC(NH_2+)NH_2$ group respectively.

Esterified carboxyl groups represented by the group $R^8$ include groups of formula —$CO_2Alk^2$ wherein $Alk^2$ is a straight or branched, optionally substituted $C_{18}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyloxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the $Alk^2$ group include $R^8$ substituents described above.

When $Alk^1$ is present in or as a substituent $R^7$ it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupred by one, two, or three —O— or —S—, atoms or —$S(O)$—, —$S(O)_2$— or —$N(R^{10})$— groups.

Aryl or heteroaryl groups represented by the groups $R^8$ or $R^9$ include mono- or bicyclic optionally substituted $C_{6-12}$ aromatic or $C_{1-9}$ heteroaromatic groups as described above for the group Ar. The aromatic and heteroaromatic groups may be attached to the remainder of the compound of formula (1) by any carbon or hetero e.g. nitrogen atom as appropriate.

Particularly useful atoms or groups represented by $R^7$ include fluorine, chlorine, bromine or iodine atoms, or $C_{1-6}$alkyl, e.g. methyl or ethyl, $C_{1-6}$alkylamino, e.g. methylamino or ethylamino, $C_{1-6}$ hydroxyalkyl, e.g. hydroxymethyl or hydroxyethyl, $C_{1-6}$alkylthiol e.g. methylthiol or ethylthiol, $C_{1-6}$alkoxy, e.g. methoxy or ethoxy, $C_{5-7}$cycloalkoxy, e.g. cyclopentyloxy, halo$C_{1-6}$alkyl, e.g. trifluoromethyl, $C_{1-6}$alkylamino, e.g. methylamino or ethylamino, amino (—$NH_2$), amino$C_{1-6}$alkyl, e.g. aminomethyl or aminoethyl, $C_{1-6}$dialkylamino, e.g. dimethylamino or diethylamino, imido, such as phthalimido or naphthalimido, e.g. 1,8-naphthalimido, 1,1,3-trioxobenzo-[d]thiazolidino, nitro, cyano, hydroxyl (—OH), formyl [HC(O)—], carboxyl (—$CO_2H$), —$CO_2Alk^2$ [where $Alk^2$ is as defined above], $C_{1-6}$ alkanoyl e.g. acetyl, thiol (—SH), thio$C_{1-6}$alkyl, e.g. thiomethyl or thioethyl, —SC(NH$_2$+)NH$_2$, sulphonyl (—SO$_3$H), $C_{1-6}$alkylsulphonyl, e.g. methylsulphonyl, aminosulphonyl (—SO$_2$NH$_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido (—CONH$_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, sulphonylamino (—NHSO$_2$H), $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, optionally substituted phenylsulphonylamino, e.g. 2-, 3- or 4-substituted phenylsulphonylamino such as 2-nitrophenylsulphonylamino, aminosulphonylamino (—NHSO$_2$NH$_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, phenylaminosulphonylamino, $C_{1-6}$alkanoylamino, e.g. acetylamino, $C_{1-6}$alkanoylamino$C_{1-6}$alkyl, e.g. acetylaminomethyl, $C_{1-6}$alkoxycarbonylamino, e.g. methoxycarbonylamino, ethoxycarbonylamino or t-butoxycarbonylamino or optionally substituted benzyloxy groups.

Where desired, two $R^7$ substituents may be linked together to form a cyclic group such as a cyclic ether, e.g. a $C_{1-6}$alkylenedioxy group such as methylenedioxy or ethylenedioxy.

It will be appreciated that where two or more $R^7$ substituents are present, these need not necessarily be the same atoms and/or groups.

Linker groups represented by the group Z in compounds of formula (1) include groups of formula -(Alk$^3$)r(L$^5$)S(L$^6$)t(Alk$^4$)$_u$— where Alk$^3$ and Alk$^4$ which may be the same or different is each an optionally substituted straight or branched $C_{1-6}$alkylene, $C_{2-6}$alkenylene or $C_{2-6}$alkynylene chain, optionally interrupted by one or more heteroatoms or heteroatom-containing groups, $L^5$ and $L^6$ is each an —O— or —S—atom or a —S(O)—, —S(O)$_2$—, —N(R$^{10}$)—, —C(O)—, —C(S)—, —C(NR$^{10}$)—, —CON(R$^{10}$)—, —CSN(R$^{10}$)—, —N(R$^{11}$)SO—, —N(R$^1$l)SO$_2$—, —N(R$^{11}$)SO$_2$N(R$^{11}$)—, —N(R$^{10}$)SON(R$^{10}$), or —N(R$^{10}$)CON(R$^{10}$) group and r, s, t and u which may the the same or different is each zero or the integer 1, provided that when one of r, s, t or u is zero at least one of the remainder is the integer 1. It will be appreciated that when an $L^5$ and $L^6$ atom or group are present, such atoms or groups are adjacent to one another and, for example form a group —N(R$^{10}$)C(NR$^{10}$)— or —OCON(R$^{10}$)—.

The heteroatoms which may interrupt the Alk$^3$ or Alk$^4$ chains include for example —O— or —S—atoms. Particular heteroatom-containing groups which may interrupt Alk$^3$ or Alk$^4$ include oxygen-, sulphur- or nitrogen-containing groups such as —S(O)—, —S(O)$_2$, or —N(R$^{10}$)— groups.

Optional substituents which may be present on Alk$^3$ or Alk$^4$ chains include halogen atoms such as chlorine, fluorine, bromine or iodine atoms and $C_{1-3}$alkyl groups such as methyl or ethyl groups. Particular examples of linker groups Z include optionally substituted —CH$_2$—, —(CH$_2$)$_2$—, or —CH$_2$)$_3$— groups, especially —CH$_2$—CH(CH$_3$)—, —CH(CH$_3$)CH$_2$—, —CH$_2$C(CH$_3$)$_2$— or —C(CH$_3$)$_2$CH$_2$— groups, —CH$_2$S—, —SCH$_2$, —CH$_2$O— or —OCH$_2$— groups. When A together with X and Y in compounds of formula (1) forms an optionally substituted monocyclic or bicyclic aromatic group [i.e. when X and Y is each a carbon atom] the aromatic group may be an optionally substituted monocyclic or bicyclic $C_{6-12}$aromatic group such as an optionally substituted phenyl, 1- or 2-naphthyl or indenyl group.

In compounds of formula (1) when A together with X and Y forms an optionally substituted monocyclic or bicyclic heteroaromatic group [i.e. X and Y is each a -carbon or nitrogen atom], the heteroaromatic group may be an optionally substituted monocyclic or bicyclic $C_{1-9}$ heteroaromatic group containing for example one, two, three or four heteroatoms selected from oxygen, sulphur or nitrogen atoms. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example nine- to thirteen-membered heteroaromatic groups containing one, two or more heteroatoms selected from oxygen, sulphur or nitrogen atoms.

Particular examples of heteroaromatic groups represented by A, X and Y together include optionally substituted pyrrolyl, furyl, thienyl, imidazolyl, N-methylimidazolyl, N-ethyl-imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, benzotriazolyl, isobenzothienyl, indolyl, isoindolyl, benzimidazolyl, imidazo[1,2-a]pyridyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl and 5,6,7,8-tetrahydroisoquinolinyl.

Optional substituents which may be present on aromatic or heteroaromatic groups represented by A, X and Y together include one, two, three or more substituents selected from fluorine, chlorine, bromine or iodine atoms, or $C_{1-6}$alkyl, e.g. methyl or ethyl, $C_{1-6}$alkylamino, e.g. methylamino or ethylamino, $C_{1-6}$ hydroxyalkyl, e.g. hydroxymethyl or hydroxyethyl, $C_{1-6}$alkylthiol e.g. methylthiol or ethylthiol, $C_{1-6}$alkoxy, e.g. methoxy or ethoxy, halo$C_{1-6}$alkyl, e.g. trifluoromethyl, halo$C_{1-6}$alkoxy, e.g. difluoromethoxy, $C_{1-6}$alkylamino, e.g. methylamino or ethylamino, amino (—NH$_2$), amino$C_{1-6}$alkyl, e.g. aminomethyl or aminoethyl, $C_{1-6}$dialkylamino, e.g. dimethylamino or diethylamino, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, phenyl, furyl, nitro, cyano, hydroxyl (—OH), formyl [HC(O)—], carboxyl (—$CO_2H$), —$CO_2Alk^1$ [where $Alk^1$ is as defined above], $C_{1-6}$ alkanoyl e.g. acetyl, thiol (—SH), thio$C_{1-6}$alkyl, e.g. thiomethyl or thioethyl, —SC(NH$_2$+)NH$_2$, sulphonyl (—SO$_3$H), $C_{1-6}$alkylsulphonyl, e.g. methylsulphonyl, aminosulphonyl (—SO$_2$NH$_2$), $C_{1-6}$alkylaminosulphonyl, e.g. methylaminosulphonyl or ethylaminosulphonyl, $C_{1-6}$ dialkylaminosulphonyl, e.g. dimethylaminosulphonyl or diethylaminosulphonyl, phenylaminosulphonyl, carboxamido (—CONH$_2$), C$_{1-6}$alkylaminocarbonyl, e.g. methylaminocarbonyl or ethylaminocarbonyl, C$_{1-6}$dialkylaminocarbonyl, e.g. dimethylaminocarbonyl or diethylaminocarbonyl, sulphonylamino (—NHSO$_2$H), C$_{1-6}$alkylsulphonylamino, e.g. methylsulphonylamino or ethylsulphonylamino, C$_{1-6}$dialkylsulphonylamino, e.g. dimethylsulphonylamino or diethylsulphonylamino, optionally substituted phenylsulphonylamino, e.g. 2-, 3- or 4-substituted phenylsulphonylamino such as 2-nitrophenylsulphonylamino, aminosulphonylamino (—NHSO$_2$NH$_2$), C$_{1-6}$alkylaminosulphonylamino, e.g. methylaminosulphonylamino or ethylaminosulphonylamino, C$_{1-6}$dialkylaminosulphonylamino, e.g. dimethylaminosulphonylamino or diethylaminosulphonylamino, phenylaminosulphonylamino, C$_{1-6}$alkanoylamino, e.g. acetylamino, C$_{1-6}$ alkanoylaminoC$_{1-6}$alkyl, e.g. acetylaminomethyl, or C$_{1-6}$alkoxycarbonylamino, e.g. methoxycarbonylamino, ethoxycarbonylamino or t-butoxycarbonylamino groups.

Where desired, two of these substituents may be linked together to form a cyclic group such as a cyclic ether, e.g. a C$_{1-6}$alkylenedioxy group such as a methylenedioxy or ethylenedioxy group.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

It will be appreciated that where compounds of formula (1) exist as geometrical isomers and/or enantiomers or diasteromers then the invention extends to all such isomers of the compounds of formula (1), and to mixtures thereof, including racemates.

One particularly useful group of compounds according to the invention is that wherein Ar is an optionally substituted aromatic group. Particularly useful compounds of this type are those wherein Ar is an optionally substituted phenyl group. In compounds of this type Ar may be in particular a phenyl group or a phenyl group substituted by one or two R$^7$ groups as defined herein.

In another preference, A together with X and Y is preferably an optionally substituted phenyl group, the optional substituents being those previously generally and particularly described above in relation to aromatic or heteroaromatic groups represented by A, X and Y together. In one particular preference, A together with X and Y is preferably a phenyl or monosubstituted phenyl group in which the substituent is one of those just mentioned. Particularly useful substituents of these types include methoxy groups.

Z in compounds of formula (1) is preferably an optionally substituted —(CH$_2$)$_2$ group. Particular examples of groups of this type include —(CH$_2$)$_2$—, —CH$_2$CH(CH$_3$)— or —CH$_2$C(CH$_3$)$_2$— groups. In general compounds of formula (1) in which Z is —CH$_2$C(CH$_3$)$_2$— are particularly useful.

In general in compounds of formula (1), and in the above-mentioned preferences, the group R$^1$ is preferably a group —L$^1$ R$^2$ where L$^1$ is a covalent bond or an oxygen atom. R$^2$ in general is preferably an (Alk)$_m$R$^3$ group in which Alk, m and R$^3$ are as defined for formula (1). In compounds of these types Alk when present is preferably a C$_{1-6}$alkylene chain, especially an ethylene chain. R$^3$ is preferably present in R$^2$ as a heterocycloaliphatic group of the type generally described above, and especially is an optionally substituted C$_{3-7}$ cycloalkyl group containing one or two heteroatoms. Particularly important groups of these types include C$_4$ heterocycloalkyl groups, particularly optionally substituted pyrrolidinyl, morpholinyl or piperazinyl groups, especially where these are attached to the remainder of the molecule through their nitrogen atoms. Optionally substituted pyrrolidinyl or piperazinyl groups are especially useful.

Particularly useful compounds according to the invention include:

6,6-Dimethyl-9-methoxy-N-[3-(2-pyrrolidinoethoxy) phenyl]benzoth]-5,6-dihydroquinazoline-2-amine hydrochloride;

6,6-Dimethyl-9-methoxy-N-[4-(4-methylpiperazin-1-yl]-benzo[h]-5,6-dihydroquinazoline-2-amine;

and the salts, solvates and hydrates thereof

Compounds according to the invention are potent and selective inhibitors of protein kinases, especially those of the src family, as demonstrated by their inhibition of enzymes, such as p56$^{lck}$ and p59$^{fyn}$. The ability of the compounds to act in this way may be simply determined by the tests described in the Examples hereinafter.

The compounds according to the invention are thus of particular use in the prophylaxis and treatment of diseases in which inappropriate protein tyrosine kinase action plays a role, for example in autoimmune diseases such as rheumatoid arthritis, multiple sclerosis, and systemic lupus erythematosus, in transplant rejection, in graft v host disease, in hyperproliferative disorders such as tumours, psoriasis, in pannus formation in rheumatoid arthritis, restenosis following angioplasty and atherosclerosis, in osteoporosis and in diseases in which cells receive pro-inflammatory signals such as asthma, inflammatory bowel disease and pancreatitis.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around long/kg to 50 mg/kg body weight for parenteral administration and around 0.05 mg to around 1000 mg e.g. around 0.5 mg to around 1000 mg for nasal administration or administration by insufflation.

The compounds of the invention may be prepared by a number of processes as generally described below and more specifically in the examples hereinafter. In the following process description, the symbols $R^1$, Ar, X, Y, Z and A when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of a compound of formula (1) and the processes according to the invention described hereinafter are to be understood to extend to such removal of protecting groups.

Thus according to a further aspect of the invention, a compound of formula (1) may be prepared by reaction of a guanidine of formula (2):

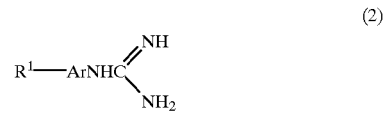

(2)

or a salt thereof with an enaminone of formula (3):

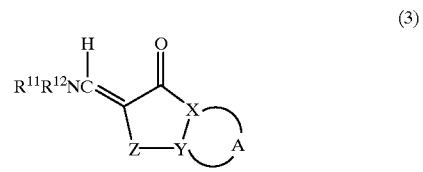

(3)

where $R^{11}$ and $R^{12}$, which may be the same or different is each a $C_{1-6}$ alkyl group.

The reaction may be performed in a solvent, for example a protic solvent such as an alcohol, e.g. ethanol, methoxyethanol or propanol, optionally in the presence of a base e.g. an alkali metal base, such as sodium hydroxide or potassium carbonate, at an elevated temperature, e.g. the reflux temperature.

Salts of the compounds of formula (2) include acid salts such as inorganic acid salts e.g. hydrochlorides or nitrates.

Intermediate guanidines of formula (2) may be prepared by reaction of the corresponding amine $R^1ArNH_2$ with cyanamide at an elevated temperature. The reaction may be performed in a solvent such as ethanol at an elevated temperature, e.g. up to the reflux temperature. Where it is desired to obtain a salt of a guanidine of formula (2), the reaction may be performed in the presence of a concentrated acid, e.g. hydrochloric or nitric acid.

The amines $R^1$ $ArNH_2$ are either known compounds or may be obtained by conventional procedures, for example by hydrogenation of the corresponding nitro derivatives using for example hydrogen in the presence of a metal catalyst in a suitable solvent, for example as more particularly described in the interconversion reactions discussed below. The derivatives $R^1ArNO_2$ for this particular reaction are either known compounds or may be prepared from known nitro derivatives using for example alkylation and other standard substitution reactions as described in the interconversion reactions hereinafter.

Intermediate enaminones of formula (3) are either known compounds or may be prepared by reaction of a ketone of formula (4):

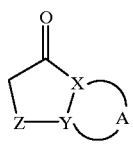

(4)

with an acetal $(R^{11})(R^{12})NCH(OCH_3)_2$ at an elevated temperature. The starting materials for this reaction are either known compounds of may be prepared by methods analogous to those used for the preparation of the known compounds.

In another process according to the invention, a compound of formula (1) wherein $R^1$ is a group —$L^1$ AlkR$^3$ where $L^1$ is a linker atom or group may be prepared by alkylation of an intermediate of formula (5):

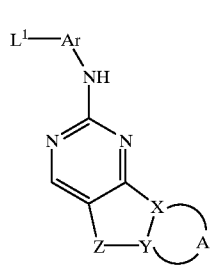

(5)

with a compound $R^3$AlkL where L is a leaving atom or group.

Particular leaving atoms or groups represented by L include for example halogen atoms, e.g. bromine, iodine or chlorine atoms, and sulphonyloxy groups, e.g. alkylsulphonyloxy groups, such as trifluoromethylsulphonyloxy, and arylsulphonyloxy groups, such as p-toluenesulphonyloxy.

The alkylation reaction may be carried out in the presence of a base, e.g. an inorganic base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as a dimethylformamide or an ether, e.g. a cyclic ether such as tetrahydrofuran, at around 0° C. to around 100° C.

Intermediates of formula (5) may be prepared by reaction of an amine $L^1$ArNH$_2$ with a compound of formula (6):

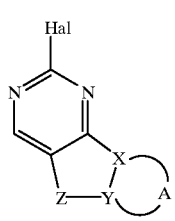

(6)

where Hal is a halogen atom such as a chlorine atom.

The reaction may be performed at an elevated temperature, for example the reflux temperature, where necessary in the presence of a solvent, for example a ketone such as acetone, an alcohol such as ethanol or 2-ethoxyethanol or an aromatic hydrocarbon such as toluene, optionally in the presence of a base, for example an organic amine such as triethylamine or pyridine, or an acid, for example an inorganic acid such as hydrochloric acid.

The intermediates of formula (6) may be prepared by heating the corresponding ketones of formula (7):

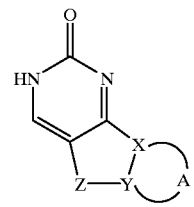

(7)

with a phosphorous oxyhalide in a solvent such as dimethylformamide at an elevated temperature such as the reflux temperature.

Ketones of formula (7) may be obtained from the corresponding amines of formula (8):

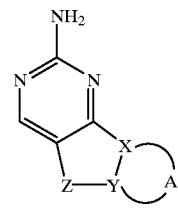

(8)

by reaction with a nitrite, e.g. sodium nitrite in an aqueous acidic solution followed by treatment with a base, for example an inorganic base such as sodium hydroxide.

Amines of formula (8) may be prepared by reaction of an enaminone of formula (3) with guanidine or a salt thereof using the reaction conditions described above for the preparation of compounds of formula (1) from compounds of formula (3).

Intermediates of formulae $R^3$AlkL and $L^1$ArNH$_2$ for use in the above reactions are either known readily available compounds or may be prepared by methods analogous to those used for the preparation of the known compounds.

In a further process according to the invention a compound of formula (1) may be prepared by displacement of the halogen atom in a compound of formula (6) with a compound of formula $R^1$ArNH$_2$ using the reagents and conditions described above for the preparation of intermediates of formula (5). The compounds of formula $R^1$ArNH$_2$ are either known or may be obtained by conventional procedures, for example by hydrogenation of the corresponding nitro derivatives using for example hyrogen in the presence of a metal catalyst for example as more particularly described in the interconversion reactions and Examples described below. The nitro derivatives are etiher readily available or may be obtained by manipulation of known nitro derivatives using for example alkylation and other standard substitution reactions described below and in the Examples.

In another example of a displacement reactiuon, a compound according to the invention in which $R^1$ is a —$L^1$AlkR$^3$ group and $R^3$ is a heterocyclic amino group attached to the remainder of the molecule through its nitrogen atom may be prepared by treating a coresponding compound in which $R^1$ is a —$L^1$AlkL group [where L is a leaving atom or group as described previously], with an amine $R^3$aNH [where $R^3$aN is an optionally substituted heterocycloaliphatic group $R^3$ containing at least one nitrogen atom]. The reaction may be carried out in a solvent, for example an amide such as dimethylformamide, optionally in the presence of a base, for example an organic amine such as pyridine, at an elevated temperature such as the reflux temperature. The polycyclic starting material for use in this reaction may be obtained by utilising any of the methods described herein, for example by alkylation of an intermediate of formula (5) with a compound AlkL or a precursor thereto.

Compounds of formula (1) may also be prepared by interconversion of other compounds of formula (1) and it is to be understood that the invention extends to such interconversion processes. Thus, for example, standard substitution approaches employing for example alkylation, arylation, acylation, thioacylation, sulphonylation, formylation or coupling reactions may be used to add new substitutents to and/or extend existing substituents in compounds of formula (1). Alternatively existing substituents in compounds of formula (1) may be modified by for example oxidation, reduction or cleavage reactions to yield other compounds of formula (1).

The following describes in general terms a number of approaches which can be employed to modify existing Ar and aromatic or heteroaromatic groups represented by groups X, Y and A together in compounds of formula (1). It will be appreciated that each of these reactions will only be possible where one or more appropriate functional groups exist in the compound of formula (1).

Thus, for example alkylation or arylation of a compound of formula (1), for example to introduce a group —Alk$_1$ ($R^8$)$_{n\ or\ R}{}^8$ where $R^8$ is an aryl group may be achieved by reaction of the compound with a reagent ($R^8$)nAlk$^1$ L or $R^8$L, where L is a leaving group as described above. The alkylation or arylation reaction may be carried out as described previously in relation to the alkylation of intermediates of formula (5).

In another general example of an interconversion process, a compound of formula (1) may be acylated or thioacylated, for example to introduce a group —C(O)$R^9$ or —C(S)$R^9$. The reaction may be performed for example with an acyl or thioacyl halide or anhydride in the presence of a base, such as an organic amine e.g. triethylamine or pyridine in a solvent such as an aromatic or halogenated hydrocarbon, e.g. toluene, optionally in the presence of a catalyst, e.g. dimethylaminopyridine dichloromethane at for example ambient up to the reflux temperature, or by reaction with a thioester in an inert solvent such as tetrahydrofuran at a low temperature such as around 0° C.

Compounds of formula (1) may be prepared in another general interconversion reaction by sulphonylation, for example by reaction of the compound with a reagent $R^9$S (O)L or $R^9$SO$_2$L where L is a leaving group as described above in the presence of a base, for example an inorganic base such as sodium hydride in a solvent such as an amide, e.g. a substituted amide such as dimethylformamide at for example ambient temperature. The reaction may in particular be performed with compounds of formula (1) in which Ar and/or X, Y and A together possesses a primary or secondary amino group.

In further examples of interconversion reactions according to the invention compounds of formula (1) may be prepared from other compounds of formula (1) by modification of existing functional groups in the latter.

Thus in one example, ester groups —CO$_2$Alk$^2$ in compounds of formula (1) may be converted to the corresponding acid [—CO$_2$H] by acid- or base-catalysed hydrolysis depending on the nature of the group Alk$^2$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol.

In a second example, —O$R^9$ [where $R^9$ represents an alkyl group such as methyl group] groups in compounds of formula (1) may be cleaved to the corresponding alcohol —OH by reaction with boron tribromide in a solvent such as a halogenated hydrocarbon, e.g. dichloromethane at a low temperature, e.g. around 78° C.

In another example, alcohol —OH groups in compounds of formula (1) may be converted to a corresponding —O$R^9$ group by coupling with a reagent $R^9$OH in a solvent such as tetrahydrofuran in the presence of a phosphine, e.g. triphenylphosphine and an activator such as diethyl-, diisopropyl-, or dimethylazodicarboxylate.

Aminosulphonylamino [—NHSO$_2$NH$_2$] groups in compounds of formula (1) may be obtained, in another example, by reaction of a corresponding amine [—NH$_2$] with sulphamide in the presence of an organic base such as pyridine at an elevated temperature, e.g. the reflux temperature.

In another example of an interconversion reaction, amine (—NH$_2$) groups may be alkylated using a reductive alkylation process employing an aldehyde and a borohydride, for example sodium triacetoxyborohyride or sodium cyanoborohydride, in a solvent such as a halogenated hydrocarbon, e.g. dichloromethane, a ketone such as acetone, or an alcohol, e.g. ethanol, where necessary in the presence of an acid such as acetic acid at around ambient temperature.

In a further example, amine [—NH$_2$] groups in compounds of formula (1) may be obtained by hydrolysis from a corresponding imide by reaction with hydrazine in a solvent such as an alcohol, e.g. ethanol at ambient temperature.

In another example, a nitro [—NO$_2$] group may be reduced to an amine [—NH$_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

In a further example, amide [—CONH$R^9$] groups in compounds of formula (1) may be obtained by coupling a corresponding acid [—CO$_2$H] or an active derivative thereof, e.g. an acid anhydride, ester, imide or halide, with an amine $R^9$NH$_2$. The reaction may also be used to obtain compounds of formula (1) in which R$_1$ is a —COR$^3$ group [where R$^3$ is an optionally substituted heterocycloaliphatic group containing at least one nitrogen atom connected to the group —CO—] by reaction of the corresponding acid in which R$^1$ is —CO$_2$H or an active derivative thereof and an amine $R^{3a}$NH as described above. The coupling reaction may be performed using standard conditions for reactions of this type. Thus for example the reaction may be carried out in a solvent, for example an inert organic solvent such as an amide, e.g. a substituted amide such as dimethylformamide, at a low temperature, e.g. −30° C. to ambient temperature, optionally in the presence of a base, e.g. an organic base such as a cyclic amine, e.g. N-methylmorpholine, and where necessary in the presence of a condensing agent, for example a diimide such as 1-(3-dimethylaminopropyl)-3-ethylcarbodiimide, advantageously in the presence of a catalyst such as a N-hydroxytriazole, e.g. 1-hydroxybenzotriazole.

Aromatic halogen substituents in compounds of the invention may be subjected to halogen-metal exchange with a base, for example a lithium base such as n-butyl or t-butyl lithium, optionally at a low temperature, e.g. around −78° C., in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyidisulphide as the electrophile.

In another example, sulphur atoms in compounds of the invention, for example when present in the linker group Z, may be oxidised to the corresponding sulphoxide using an oxidising agent such as a peroxy acid, e.g. 3-chloroperoxybenzoic acid, in an inert solvent such as a halogenated hydrocarbon, e.g. dichloromethane, at around ambient temperature.

In a still further example, compounds of the invention may be prepared by aromatisation of a corresponding hydroaromatic compound. Thus, for example, a compound of formula (1) wherein the linker group Z is a —$CH_2$—$CH_2$— chain may be treated with a hydrogen acceptor, for example a quinone such as 2,3-dichloro-5,6-dicyano-1,4-benzoquinone in a solvent such as an ether, e.g. a cyclic ether such as dioxane, at an elevated temperature, e.g. the reflux temperature, to yield a corresponding compound in which Z is a —CH=CH— chain.

In a further example of an interconversion reaction, a compound of the invention containing a substituent $R^7$ in which $R^7$ is an aryl or heteroaryl group may be prepared by coupling a corresponding compound in which the $R^7$ substituent is a halogen atom such as a bromine atom, with a boronic acid $Ar^1B(OH)_2$ [in which $Ar^1$ is an aryl or heteroaryl group as defined above for Ar] in the presence of a complex metal catalyst. Suitable catalysts include heavy metal catalysts, for example palladium catalysts such as tetrakis(triphenylphosphine) palladium. The reaction may be performed in an inert organic solvent, for example an ether such as dimethoxyethane, in the presence of a base, e.g. an alkali carbonate such as sodium carbonate, at an elevated temperature, e.g. the reflux temperature.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

The following Examples illustrate the invention.

All temperatures are in ° C. The following abbreviations are used:

THF—tetrahydrofuran; DMF—dimethylformamide; DMSO—dimethylsulphoxide; HOBt—1-hydroxy-7-azabenzotriazole; EDC—1-(3-dimethylaminopropyl)-3-ethylcarbodiimide hydrochloride;

EXAMPLE 1

9-Methoxy-N-[3-(2-pyrrolidin-1-ylethoxy)phenyl]benzo[h]-5,6-dihydroquinazoline-2-amine To a solution of N-(3-hydroxyphenyl)-9-methoxybenzo[h]-5,6-dihydroquinazoline-2-amine (250 mg, 0.78 mmol) and 1-(2-chloroethyl)pyrrolidine hydrochloride (133 mg, 0.78 mmol) in DMF (10 ml) under a nitrogen atmosphere was added caesium carbonate (562 mg, 1.7 mmol) and the resulting mixture heated at 100° for 18 h. The reaction was concentrated under reduced pressure and the resulting residue taken up in ethyl acetate washed with water, dried ($MgSO_4$) and concentrated again. The resulting orange solid was subjected to column chromatography [$SiO_2$—10% methanol-dichloromethane] to give the title compound as a yellow solid (119 mg) m.p. 130°. δH ($CDCl_3$) 8.27 (1H, s), 7.89 (1H, d, J 2.8 Hz), 7.62 (1H, t, J 2.2 Hz), 7.23 (1H, m), 7.16 (3H, m), 6.96 (1H, dd, J 8.3, 2.8 Hz), 6.59 (1H, m), 4.21 (2H, t, J 5.9 Hz), 3.91 (3H, s), 2.99 (2H, t, J 5.9 Hz), 2.85 (4H, m), 2.74 (4H, m) and 1.85 (4H, m).

The N-(3-hydroxyphenyl)-9-methoxybenzo[h]-5,6-dihydroquinazoline-2-amine used as starting material was prepared by heating a solution of 2-chloro-9-methoxybenzo[h]-5,6-dihydroquinazoline (0.3 g, 1.22 mmol) and 3-aminophenol (0.15 g, 1.34 mmol) in ethoxyethanol (3 ml) at 130° under a nitrogen atmosphere for 7 h. The reaction was concentrated under reduced pressure and the residue was triturated with water and ethyl acetate to give the desired compound as a beige solid (256 mg) m.p. 255° δH ($d^6$ DMSO) 9.38 (1H, s), 9.21 (1H, s), 8.36 (1H, s), 7.78 (1H, d, J 2.8 Hz), 7.43 (1H, m), 7.23 (2H, m), 7.03 (2H, m), 6.35 (1H, d, J 7.5 Hz), 3.83 (3H, s) and 2.80 (4H, m).

The 2-chloro-9-methoxybenzo[h]-5,6-dihydroquinazoline was prepared by heating 9-methoxybenzo[h]-5,6-dihydro-1(H)-quinazolin-2-one (28.8 g) in phosphorous oxychloride (250 ml) and DMF(10 ml) at reflux for 16 h. The reaction was concentrated under reduced pressure and the black residue poured into ice-water (600 g) and solid sodium bicarbonate added to pH 7.5. The resulting solution was extracted with dichloro-methane (×3), and the organic phase was dried ($MgSO_4$) and concentrated under reduced pressure. The residue was subjected to column chromatorgaphy (silica-ethyl acetate) to give the desired compound as a yellow solid (26.7 g) m.p. 138°.

The quinazolin-2-one was prepared by suspending 9-methoxybenzo[h]-5,6-dihydroquinazoline-2-amine (30.0 g, 132 mmol) in water (400 ml) and adding concentrated sulphuric acid (330 ml) dropwise. Sodium nitrite (24.7 g, 358 mmol) in water (300 ml) was then added dropwise with stirring and a yellow precipitate formed over 2 h. The solid was collected and stirred in 2M aqueous sodium hydroxide for 0.5 h, and the resulting solid was collected to give the desired compound as a buff solid (22.3 g) m.p. >300° (decomp). δ($d^6$ DMSO) 8.58 (1H, s), 7.56 (1H, d, J 2.6 Hz), 7.15 (1H, d, J 8.2 Hz), 6.87 (1H, d, J 8.2, 2.6 Hz), 6.72 (1H, br s) and 2.85–2.78 (4H, m).

The 9-methoxybenzo[h]-5,6-dihydroquinazoline-2-amine was prepared by adding powdered sodium hydroxide (6.24 g, 156 mmol) to a solution of guanidine carbonate (14.05 g, 78 mmol) and 3,4-dihydro-2-dimethylaminomethylene-7-methoxy-1(2H)-naphthalenone (30.0 g, 130 mmol) in isopropanol (200 ml). The resulting mixture was heated at reflux for 2 h and on cooling the precipitate was collected and washed with water and diethyl ether, to give the desired compound as a beige solid, (45.6 g) m.p. 188°. δH ($CDCl_3$) 8.14 (1H, s), 8.05 (1H, s), 7.18 (1H, dd, J 7.6, 1.3 Hz), 7.12 (1H, d, J 7.6 Hz), 4.98 (2H, br s), 2.89–2.85 (2H, m), 2.78–2.73 (2H, m) and 2.40 (3H, s).

The 3,4-dihydro-2-dimethylaminomethylene-7-methoxy-1(2H)-naphthalen-one was obtained by heating a mixture of 7-methoxy-1-tetralone (5.0 g, 28.4 mmol) and N,N-dimethylformamide diethylacetal (10 ml, 58.3 mmol) at 110° for 3 h. The reaction was allowed to cool to room temperature and excess reagent removed in vacuo to give a thick oil. This crude material was subjected to column chromatography (silica, 5% methanol in dichloromethane) to give the desired compound as a yellow solid (1.28 g), m.p. 95° MS ($ES^+$) 232 ($MH^+$, 100%).

The following compounds of Examples 2–6 were prepared in a similar manner to the compound of Example 1 using the starting materials shown:

EXAMPLE 2

9-Methoxy-N-[3-(2-morpholinoethoxy)phenyl]benzo[h]-5,6-dihydroquinazoline-2-amine From N-(3-hydroxyphenyl)-9-methoxybenzo[h]-5,6-dihydroquinazoline-2-amine (500 mg, 1.56 mmol), 4-(2-chloroethyl)morpholine hydrochloride (320 mg, 1.72 mmol) and caesium carbonate (1.1 g, 3.4 mmol) to give the title compound as a yellow solid m.p. 156°. δH (CDCl$_3$) 8.27 (1H, s), 7.88 (1H, d, J 2.8 Hz), 7.64 (1H, t, J 2.2 Hz), 7.18 (4H, m), 6.95 (1H, dd, J 8.27, 2.8 Hz), 6.58 (1H, dd, J 8.0, 2.5 Hz), 4.17 (2H, t, J 5.7 Hz), 3.90 (3H, s), 3.73 (4H, t, J 4.8 Hz), 2.85 (6H, m) and 2.58 (4H, t, J 4.7 Hz).

EXAMPLE 3

9-Methoxy-N-[4-(2-pyrrolidin-1-ylethoxy)phenyl]benzo[h]-5,6-dihydroquinazoline-2-amine From N-(4-hydroxyphenyl)-9-methoxybenzo[h]-5,6-dihydroquinazoline-2-amine (500 mg, 1.56 mmol), 1-(2-chloroethyl)pyrrolidine (260 mg, 1.56 mmol) and caesium carbonate (1.1 g, 3.4 mmol) to give the title compound as a yellow solid (117 mg), m.p. 140°. δH (CDCl$_3$) 8.22 (1H, s), 7.83 (1H, d, J 2.8 Hz), 7.58 (2H, m), 7.15 (1H, d, J 8.3 Hz), 6.93 (4H, m), 4.18 (2H, t, J 5.8 Hz), 6.93 (4H, m), 4.18 (2H, t, J 5.8 Hz), 3.89 (3H, s), 3.02 (2H, t, J 5.7 Hz), 2.81 (8H, m) and 1.88 (4H, m).

The N-(4-hydroxyphenyl)-9-methoxybenzo[h]-5,6-dihydroquinazoline-2-amine used as starting material was prepared in a similar manner to the analogous compound of Example 1, from 2-chloro-9-methoxybenzo[h]-5,6-dihydroquinazoline (300 mg, 1.22 mmol) and 4-aminophenol (146 mg, 1.34 mmol) to give the desired material as a red-brown solid (333 mg) m.p. 270°. δH (d$^6$ DMSO) 9.15 (1H, s), 8.97 (1H, s), 8.29 (1H, s), 7.71 (1H, d, J 2.7 Hz), 7.56 (2H, d, J 8.9 Hz), 7.23 (1H, d, J 8.3 Hz), 6.99 (1H, dd, J 8.3, 2.8 Hz), 6.71 (2H, d, J 8.8 Hz), 3.81 (3H, s) and 2.76 (4H, m).

EXAMPLE 4

9-Methoxy-N-[4-(2-morpholinoethoxy)phenyl]benzo[h]-5,6-dihydroquinazoline-2-amine From N-(4-hydroxyphenyl)-9-methoxybenzo[h]-5,6-dihydroquinazoline-2-amine (500 mg, 1.56 mmol), 4-(2-chloroethyl)morpholine (320 mg, 1.72 mmol) and caesium carbonate (1.1 g, 3.4 mmol) to give the title compound as a yellow solid (112 mg) m.p. 114°. δH(d$^6$ DMSO) 9.27 (1H, s), 8.32 (1H, s), 7.70 (3H, m), 7.24 (1H, d, J 8.3 Hz), 7.00 (1H, m), 6.89 (2H, d, J 9.0 Hz), 4.05 (2H, t, J 5.8 Hz), 3.82 (3H, s), 3.58 (4H, t, J 4.7 Hz), 3.27 (4H, s) and 2.76 (6H, m).

EXAMPLE 5

N-[4,5-Dimethoxy-3-(2-pyrrolidin-1-ylethoxy)phenyl]-9-methoxybenzo[h]-5,6-dihydroquinazoline-2-amine From N-(3,4-Dimethoxy-5-hydroxyphenyl)-9-methoxybenzo[h]-5,6-dihydroquinazoline-2-amine (111 mg, 0.29 mmol), 1-(2-chloroethyl)-pyrrolidine hydrochloride (75 mg, 0.47 mmol) and caesium carbonate (382 mg, 1.17 mmol) to give the title compound as a yellow solid (81 mg) m.p. 115–117°. δH (CDCl$_3$) 8.26 (1H, s), 7.85 (1H, d, J 2.8 Hz), 7.16 (1H, d, J 8.3 Hz), 7.09 (1H, d, J 2.4 Hz), 7.05 (1H, s), 6.99–6.92 (2H, m), 4.22 (2H, t, J 6.2 Hz), 3.90 (3H, s), 3.86 (3H, s), 3.83 (3H, s), 2.97 (2H, t, J 6.1 Hz), 2.90–2.78 (4H, m), 2.67 (4H, m) and 1.80 (4H, m).

EXAMPLE 6

N-[3-Chloro-5-methyl-4-(2-pyrrolidin-1-ylethoxy)phenyl]-9-methoxybenzo[h]-5,6-dihydroquinazoline-2-amine dihydrochloride From N-(3-chloro-4-hydroxy-5-methylphenyl)-9-methoxybenzo[h]-5,6-dihydroquinazoline-2-amine (150 mg, 0.37 mmol), 1-(2-chloroethyl) pyrrolidine hydrochloride (62 mg, 0.37 mmol) and caesium carbonate (238 mg, 0.73 mmol) to give the title compound as a dark yellow solid (181 mg), m.p. >90° (decomp). δH(d$^6$ DMSO) 11.08 (1H, br s), 9.72 (1H, s), 8.41 (1H, s), 8.06 (1H, d, J 2.4 Hz), 7.73 (1H, d, J 2.6 Hz), 7.53 (1H, d, J 2.4 Hz), 7.25 (1H, d, J 8.3 Hz), 7.02 (1H, dd, J 8.3, 2.6 Hz), 4.21–4.19 (2H, m), 3.85 (3H, s), 3.61–3.58 (4H, m), 3.15 (2H, m), 2.83–2.78 (4H, m), 2.49 (3H, s) and 2.03 (4H, m).

The quinazoline-2-amine used as starting material was prepared in a similar manner to the analogous compound of Example 1 from 2-chloro-9-methoxybenzo[h]-5,6-dihydroquinazoline (0.5 g, 2.0 mmol) and 4-amino-2-chloro-6-methylphenol (0.32 g, 2.0 mmol) to give the desired product as a yellow powder (270 mg) m.p. 264–266°. δH(d$^6$ DMSO) 9.95 (1H, br s), 8.39 (1H, s), 8.28 (1H, br s), 7.81 (1H, s), 7.70 (1H, d, J 2.5 Hz), 7.32 (1H, s), 7.27 (1H, d, J 8.3 Hz), 7.06 (1H, dd, J 8.3, 2.5 Hz), 3.83 (3H, s), 2.82–2.49 (4H, m) and 2.21 (3H, s).

EXAMPLE 7

9-Methoxy-N-[4-methoxy-3-(2-pyrrolidin-1-ylethoxy)phenyl]benzo[h]-5,6-dihydroquinazoline-2-amine To a suspension of sodium hydride (60% oil dispersion) (171 mg, 4.28 mmol) in DMF under a nitrogen atmosphere at 0°, was added N-(3-hydroxy-4methoxyphenyl)-9-methoxybenzo[h]-5,6-dihydroquinazoline-2-amine (400 mg, 1.07 mmol) and the mixture stirred for 10 min. After this time 1-(2-chloroethyl)pyrrolidine (273 mg, 1.60 mmol) was added and the reaction temperature elevated to 100° for 5 h. The reaction was concentrated in vacuo and the resulting residue taken up in ethyl acetate, washed with water, dried (MgSO$_4$) and again concentrated. The residue was subjected to column chromatography (silica gel—10% methanoldichloromethane) to afford the title compound as a yellow solid (82 mg) m.p. 133°. δH (CDCl$_3$) 8.23 (1H, s), 7.89 (1H, d, J 2.8 Hz), 7.51 (1H, d, J 2.5 Hz), 7.14 (2H, m), 7.00 (1H, s), 6.94 (1H, dd, J 8.3, 2.8 Hz), 6.86 (1H, d, J 8.7 Hz), 4.31 (2H, t, J 5.9HZ), 3.87 (3H, s), 3.84 (3H, s), 3.14 (2H, t, J 5.8 Hz), 2.80 (8H, m) and 1.89 (4H, m).

The quinazoline-2-amine used as starting material was prepared in a similar manner to the analogous compound of Example 1, from 2-chloro-9-methoxybenzo[h]-5,6-dihydroquinazoline (1.0 g, 4.06 mmol) and 5-amino-2-methoxyphenol (0.57 g, 4.06 mmol) to give the desired product (954 mg) as an orange solid, m.p. 251°. δH(d$^6$ DMSO) 10.02 (1H, br s), 8.36 (1H, s), 7.72 (1H, d, J 2.8 Hz), 7.27 (2H, m), 7.07 (2H, m), 6.91 (1H, d, J 8.7 Hz), 3.81 (3H, s), 3.75 (3H, s) and 2.82 (4H, m).

EXAMPLE 8

9-Methoxy-N-[3-methoxy-4-(2-pyrrolidin-1-ylethoxy)phenyl]benzo[h]-5,6-dihydroquinazoline-2-amine From N-(4-hydroxy-3-methoxyphenyl)-9-methoxybenzo[h]-5,6-dihydroquinazoline-2-amine (500 mg, 1.29 mmol), 1-(2-chloroethyl)pyrrolidine (331 mg, 1.95 mmol) and sodium hydride (60% oil dispersion) (208 mg, 5.19 mmol) in a similar manner to the compound of Example 7 to give the title compound as a yellow solid (273 mg) m.p. 131°. δH (CDCl$_3$) 8.24 (1H, s), 7.85 (1H, d, J 2.7 Hz), 7.53 (1H, d, J 2.4 Hz), 7.16 (1H, d, J 8.4 Hz), 7.35 (2H, m), 6.98 (2H, m), 4.22 (2H, t, J 6.1 Hz), 3.91 (3H, s), 3.87 (3H, s), 3.07 (2H, t, J 6.1 Hz), 2.86 (8H, m) and 1.89 (4H, m).

The quinazoline-2-amine used as starting material was prepared in a similar manner to the analogous compound of Example 1, from 2-chloro-9-methoxybenzo[h]-5,6-dihydroquinazoline (1.0 g, 4.06 mmol) and 4-amino-2-methoxyphenol (565 mg, 4.06 mmol) to give the desired product (1.01 g) as a dark yellow solid m.p. 258°. δH(d$^6$ DMSO) 9.96 (1H, br s), 8.34 (1H, s), 7.70 (1H, d, J 2.8 Hz), 7.37 (1H, d, J 2.2 Hz), 7.30 (1H, d, J 8.4 Hz), 7.10 (1H, dd, J 8.3, 2.8 Hz), 7.04 (1H, dd, J 8.5, 2.4 Hz), 6.78 (1H, d, J 8.5 Hz), 3.80 (3H, s), 3.77 (3H, s) and 2.82 (4H, m).

EXAMPLE 9

N-[3,5-Dimethyl-4-(2-pyrrolidin-1-ylethoxy)phenyl]-9-methoxybenzo[h]-5,6-dihydroquinazoline-2-amine A solution of 2-chloro-9-methoxybenzo[h]-5,6-dihydroquinazoline (50 mg, 0.20 mmol) and 1-[2-(4-amino-2,6-dimethylphenoxy)ethyl]pyrrolidine (47 mg, 0.20 mmol) in ethoxyethanol (2 ml) was treated with hydrogen chloride (0.2 ml of 1.0M HCl in diethyl ether, 0.20 mmol). The resulting mixture was heated at reflux for 6 h, then allowed to cool to room temperature. The mixture was partitioned between ethyl acetate and saturated aqueous sodium bicarbonate, the organic phase dried (MgSO$_4$) and evaporated. The residue was subjected to column chromatography (3–6% methanol-dichloromethane) to afford the title compound as an off-white solid (37 mg) m.p. 123–126°. δH(d$^6$ DMSO) 9.28 (1H, s), 8.36 (1H, s), 7.76 (1H, d, J 2.8 Hz), 7.51 (2H, s), 7.26 (1H, d, J 8.3 Hz), 7.01 (1H, dd, J 8.3, 2.8 Hz), 3.85 (3H, s), 3.82 (2H, m), 3.31–2.60 (1H, m), 2.23 (6H, s) and 1.73 (4H, m). 1-[2-(4-amino-2,6-dimethylphenoxy)ethyl]pyrrolidine was prepared by treating a degassed stirring solution of 1-[2-(2,6-dimethyl-4-nitrophenoxy)ethyl]pyrrolidine (824 mg, 3.12 mmol) in ethanol (8 ml) with ammonium formate (590 mg, 9.36 mmol) and 10% palladium on charcoal (100 mg) for 8 h. The mixture was filtered through Celite® and evaporated. The residue was subjected to column chromatography (2–6% methanoldichloromethane) to afford the desired product (489 mg) as a pale yellow oil. 8H (CDCl$_3$) 6.33 (2H, s), 3.84 (2H, t, J 6.3 Hz), 3.38 (2H, br s), 2.90 (2H, t, J 6.3 Hz), 2.65 (4H, m), 2.20 (6H, s) and 1.83 (4H, m). MS (ES$^+$) 235 (MH$^+$)

1-[2-(2,6-dimethyl-4-nitrophenoxy)ethyl]pyrrolidine was prepared in a manner analogous to the alkylation described in Example 1, from 2,6-dimethyl-4-nitrophenol (1.0 g, 5.98 mmol), 1-(2-chloroethyl)pyrrolidine hydrochloride (1.52 g, 8.97 mmol) and caesium carbonate (5.83 g, 17.94 mmol) to give the desired product as a brown oil. 6H (CDCl$_3$) 7.89 (2H, s), 3.96 (2H, t, J 6.1 Hz), 2.93 (2H, t, J 6.1 Hz), 2.65 (4H, m), 2.35 (6H, s) and 1.83 (4H, m). MS (ES$^+$) 265 (MH$^+$).

EXAMPLE 10

N-[3,5-Dimethyl-4-(2-morpholinoethoxy)phenyl]-9-methoxybenzofh]-5,6-dihydroquinazoline-2-amine.

From N-(3,5-dimethyl-4-hydroxyphenyl)-9-methoxybenzo[h]-5,6-dihydroquinazoline-2-amine hydrochloride (244 mg, 0.64 mmol), 2-morpholino-ethylchloride hydrochloride (142 mg, 0.76 mmol) and caesium carbonate (832 mg, 2.56 mmol) in a similar manner to the compound of Eample 1 to give the title compound as an off-white solid (112 mg), m.p. 135–137°. δH (CDCl$_3$) 8.24 (1H, s), 7.86 (1H, d, J 2.8 Hz), 7.36 (2H, s), 7.16 (1H, d, J 8.3 Hz), 6.95 (2H, m), 3.91(3H, s), 3.89 (2H, m), 3.77 (4H, m), 2.78–2.88 (6H, m), 2.59 (4H, m) and 2.31 (6H, s).

The quinazoline-2-amine used as starting material was prepared in a similar manner to the analogous compound of Example 1, from 2-chloro-9-methoxybenzo[h]-5,6-dihydroquinazoline (1.03 g, 4.20 mmol) and 2,6-dimethyl-4-aminophenol (0.63 g, 4.60 mmol) to give the desired product (0.91 g) as a red brown solid. m.p. >250°. δH(d$^6$ DMSO) 10.14 (1H, br s), 8.36 (1H, s), 8.30–7.40 (2H, br s), 7.69 (1H, s), 7.31 (1H, d, J 8.5 Hz), 7.24 (2H, s), 7.11 (1H, brs), 3.82 (3H, s), 2.86–2.79 (4H, m) and 2.19 (6H, s).

EXAMPLE 11

N-[3,5-Dimethoxy-4-(2-pyrrolidin-1-ylethoxy)phenyl]-9-methoxybenzo[h]-5,6-dihydroquinazolin-2-amine hydrochloride In a manner similar to Example 9, from 2-chloro-9-methoxybenzo[h]-5,6-dihydroquinazoline (200 mg, 0.75 mmol) and 1-[2-(4-amino-2,6-dimethoxyphenoxy)ethyl] pyrrolidine (185 mg, 0.75 mmol) and to give the title compond as a yellow solid (54 mg). m.p. 206–208°. δH (CDCl$_3$) 8.26 (1H, s), 7.85 (1H, d, J 2.7 Hz), 7.70–7.15 (2H, m), 7.04 (2H, s), 6.93 (1H, dd, J 8.3, 2.7 Hz), 4.27 (2H, t, J 4.9 Hz), 3.89 (6H, s), 3.85 (3H, s), 3.27 (6H, m), 2.87–2.80 (4H, m) and 2.04 (4H, m).

The 1-[2-(4-amino-2,6-dimethoxyphenoxy)ethyl] pyrrolidine used as starting material was prepared by treating a solution of 1-[2-(4-nitro-2,6-dimethoxyphenoxy)ethyl] pyrrolidine (230 mg, 0.78 mmol) in ethanol (5 ml) with ammonium formate (196 mg, 3.1 mmol) and 10% palladium on charcoal for 7 h. The reaction was filtered through Celite® and concentrated under reduced pressure. The residue was triturated with ether and hexane to give the desired product as an off-white solid (225 mg) m.p. 59–61°.

1-[2-(4-nitro-2,6-dimethoxyphenoxy)ethyl]pyrrolidine was prepared from 4-nitro-2,6-dimethoxyphenol [R F Collins and M Davis, J. Chem. Soc. 1863, (1961)] (0.4 g, 2.39 mmol), 1-(2-chloroethyl)pyrrolidine (612 mg, 0.36 mmol) and caesium carbonate (2.3 g, 0.72 mmol) to give the desired product as a brown oil (232 mg). MS (ES$^+$) 297 (MH$^+$).

EXAMPLE 12

N-[3,5-Dimethoxy-4-(2-morpholinoethoxy)phenyl]-9-methoxybenzo[h]-5,6-dihydroquinazoline-2-amine To a solution of morpholine (0.05 ml, 0.52 mmol) and triethylamine (0.07 ml, 0.52 mmol) in DMF (5 ml) at room temperature was added N-{3,5-dimethoxy-4-[2-(4-toluenesulphonyl)oxyethoxy]phenyl}-9-methoxybenzo[h]-5,6-dihydroquinazoline-2-amine (275 mg, 0.48 mmol) and the reaction temperature was then elevated to 60° for 12 h. The reaction was concentrated under reduced pressure and the residue columned (silica gel, 5% methanol-dichloromethane) to give the title compound as a yellow solid (51 mg) m.p. 100–102°. δH (CDCl$_3$) 8.26 (1H, s), 7.86 (1H, d, J 2.7 Hz), 7.17 (1H, d, J 8.4 Hz), 7.05 (2H, s), 6.94 (1H, dd, J 8.3, 2.8 Hz), 4.08 (2H, t, J 5.8 Hz), 3.88 (6H, s), 3.86 (3H, s), 3.76 (4H, t, J 4.7 Hz), 2.89-2.80 (4H, m), 2.78 (2H, t, J 5.9 Hz) and 2.76 (4H, m).

The N-{3,5-dimethoxy-4-[2-(4-toluenesulphonyl) oxyethoxy]phenyl}-9-methoxybenxo[h]-5,6-dihydroquinazoline-2-amine used as starting material was prepared by treating a solution of N-[3,5-dimethoxy-4-(2-hydroxy-ethoxy)phenyl]-9-methoxybenzo[h]-5,6-dihydroquinazoline-2-amine (320 mg 0.76 mmol) in dichloromethane (5 ml) with 4-toluenesulphonyl chloride (158 mg, 0.83 mmol) at ambient temperature. The reaction was washed with saturated brine (2×50 ml), the organic phase dried (MgSO$_4$) and concentrated under reduced pressure to give the desired product as a yellow solid (287 mg). 8H (CDCl$_3$) 8.27 (1H, s), 7.82 (1H, d, J 2.7 Hz), 7.8 (2H, d, J 9.0 Hz), 7.30 (2H, d, J 9.0 Hz), 7.18 (1H, d, J 8.4 Hz), 7.11 (1H, s), 7.02 (2H, s), 6.96 (1H, dd, J 8.4, 2.7 Hz), 4.32 (2H, t, J 5.0 Hz), 4.18 (2H, t, J 4.9 Hz), 3.89 (3H, s), 3.88 (6H, s), 2.95–2.79 (4H, m) and 2.41 (3H, s).

The alcohol used as starting material was obtained from 2-(4-amino-2,6-dimethoxyphenoxy)ethanol (320 mg, 1.5 mmol) and 2-chloro-9-methoxybenzo[h]-5,6-dihydroquinazoline (406 mg, 1.65 mmol) to give the desired compound as a yellow solid (331 mg). 8H (CDCl$_3$) 8.27 (1H, s), 7.85 (1H, d, J 2.8 Hz), 7.25 (1H, s), 7.17 (1H, d, J 8.3 Hz), 7.07 (2H, s), 6.94 (1H, dd, J 8.3,2.8 Hz), 4.13 (2H, t, J 4.3 Hz), 3.90 (6H, s), 3.82 (3H, s), 3.73 (2H, m), 3.54 (1H, br s), 2.89–2.78 (4H, m).

The aniline used as starting material was obtained from 2-(4-nitro-2,6-dimethoxyphenoxy)ethanol (156 mg, 0.64 mmol), ammonium formate (300 mg, 4.8 mml) and 10% palladium on carbon (40 mg) to give the desired product as a pale pink solid (90 mg) m.p. 80–82°.

2-(4-Nitro-2,6-dimethoxyphenoxy)ethanol was obtained by the treatment of a solution of potassium 4-nitro-2,6-dimethylphenoxide (300 mg, 1.27 mmol) in DMF (5 ml) with bromoethanol (0.2 ml, 2.80 mmol) at 1300 for 36 h. The reaction was concentrated in vacuo and the residue subjected to column chromatography [silica gel-ethyl acetate] to give the desired compound as a yellow solid (1 56 mg) m.p. 98–100°.

EXAMPLE 13

N-[3,5-Dichloro-4-(2-pyrrolidin-1-ylethoxy)phenyl]-9-methoxybenzo-[h]-5,6-dihydroquinazoline-2-amine From N-(3,5-dichloro-4-hydroxyphenyl)-9-methoxybenzo[h]-5,6-dihydroquinazoline-2-amine (250 mg, 0.64 mmol), 1-(2-chloroethyl)pyrrolidine hydrochloride (131 mg, 0.77 mmol) and caesium carbonate (8.34 mg, 2.56 mmol) in a similar manner to the compound of Example 1 to give the title compound as an off-white solid (167 mg), m.p. 131–133°. δH (CDCl$_3$) 8.27 (1H, s), 7.84 (1H, d, J 2.7 Hz), 7.78 (2H, s), 7.16 (1H, d, J 8.3 Hz), 7.12 (1H, s), 6.98 (1H, dd, J 8.3, 2.7 Hz), 4.16 (2H, t, J 5.9 Hz), 3.94 (3H, s), 3.03 (2H, t, J 5.9 Hz), 2.90–2.77 (1H, m) and 1.87 (4H, m).

The quinazoline-2-amine used as starting material was prepared from 2-chloro-9-methoxybenzo[h]-5,6-dihydroquinazoline (0.5 g, 2.03 mmol) and 2,6-dichloro-4-aminophenol (0.4 g, 2.23 mmol) to give the desired product (7.87 mg) as a brown powder m.p. 215–216°. δH (d$^6$ DMSO) 9.74 (1H, s), 8.42 (1H, s), 7.92 (2H, s), 7.73 (1H, d, J 2.7 Hz), 7.27 (1H, d, J 8.3 Hz), 7.04 (1H, dd, J 8.3, 2.7 Hz), 3.86 (3H, s) and 2.85–2.78 (4H, m).

EXAMPLE 14

N-[3,5-Dimethyl-4-(2-morpholinoethoxy)phenyl]-9-methoxybenzo[h]-6-thia-5,6-dihydroquinazoline-2-amine Powdered sodium hydroxide (92 mg, 2.29 mmol) was added to a solution of 3,5-dimethyl-4-(2-morpholinoethoxy) phenylguanidinium dinitrate (400 mg, 1.04 mmol) and 3,4-dihydro-2-(dimethylaminomethylene)-7-methoxy-4-thia-1 (2H)-naphthalenone (258 mg, 1.04 mmol) in propan-2-ol (5 ml) and the mixture heated at reflux for 6 h. On cooling to room temperature, the resultant precipitate was collected by filtration and washed with diethyl ether to give the title compound as a beige solid (116 mg) m.p. 127–129°. δH (CDCl$_3$) 8.27 (1H, s), 7.91 (1H, d, J 2.9 Hz), 7.32 (2H, s), 7.26 (1H, m), 7.00 (1H, br s), 6.95 (1H, dd, J 8.5, 2.9 Hz), 3.89 (5H, m), 3.83 (2H, s), 3.77 (4H, m), 2.80 (2H, t, J 4.7 Hz), 2.60 (4H, m) and 2.31 (6H, s).

The guanidine starting material was prepared by heating a mixture of 4-[2-(4-amino-2,6-dimethylphenoxy)ethyl] morpholine (1.5 g, 6.0 mmol), cyanamide (403 mg, 9.6 mmol), dissolved in water (1 ml) and concentrated nitric acid (0.79 ml, 12.0 mmol) in ethanol (7 ml), at reflux for 3 h. The reaction was concentrated under reduced pressure and the resulting residue triturated with methanol-diethyl ether at 0° to give the desired product as a grey-beige solid (2.0 g), m.p. 145°. δH(d$^6$ DMSO) 10.00 (1 h, br s), 9.41 (1H, br s), 7.26 (4H, br s), 6.93 (2H, s), 4.05–3.16 (12H, m) and 2.26 (6H, s).

The aniline used as starting material was obtained from 4-[2-(4-nitro-2,6-dimethylphenoxy)ethyl]morpholine (5.0 g, 17.86 mmol), ammonium formate (3.37 g, 53.57 mmol) and 10% palladium on carbon to give the desired product as an off-white solid (4.0 g), m.p. 103–105°. δH (CDCl$_3$) 6.34 (2H, s), 3.82 (2H, t, J 5.9 Hz), 3.75 (4H, m), 3.38 (2H, br s), 2.76 (2H, t, J 5.9 Hz), 2.57 (4H, m) and 2.19 (6H, s).

The nitrobenzene starting material was prepared from 2,6-dimethyl-4-nitrophenol (4.0 g, 23.95 mmol), 4-(2-chloroethyl)morpholine hydrochloride (6.68 g, 35.93 mmol) and caesium carbonate (23.46 g, 72 mmol) to give the desired product as a beige solid (6.6 g), m.p. 74–76°. δH (CDCl$_3$) 7.91 (2H, s), 3.95 (2H, t, J 5.7 Hz), 3.74 (4H, m), 2.80 (2H, t, J 5.7 Hz), 2.58 (4H, m) and 2.36 (6H, s).

EXAMPLE 15

N-[3,5-Dimethyl-4-(2-morpholinoethoxy)phenyl]-9-methoxy-6,6-dimethylbenzo[h]-5,6-dihydroquinazoline-2-amine From 3,5-dimethyl-4-(2-morpholinoethoxy) phenylguanidinium dinitrate (386 mg, 1.0 mmol), 3,4-dihydro-4,4-dimethyl-2-(dimethylaminomethylene)-7-methoxy-1 (2H)-naphthalenone (259 mg, 1.0 mmol) and powdered sodium hydroxide (80 g, 2.0 mmol) in a similar manner to the compound of Example 14 to give the title compound as a yellow solid (87 mg), 81–85°. δH (CDCl$_3$) 8.22 (1H, s), 7.91 (1H, d, J 2.7 Hz), 7.37 (2H, s), 7.33 (1H, d, J 8.6 Hz), 7.07 (1H, br s), 7.01 (1H, dd, J 8.5, 2.7 Hz), 3.90 (3H, s), 3.89 (2H, m), 3.77 (4H, t, J 4.4 Hz), 2.79 (2H, t, J 5.7 Hz), 2.69 (2H, s), 2.60 (4H, m), 2.31 (6H, s) and 1.28 (6H, s).

The 3,4-dihydro-4,4-dimethyl-2-dimethylaminomethylene-7-methoxy-1 (2H) naphthalenone was prepared from 4,4-dimethyl-7-methoxy-1-tetralone [2.3 g; H. Hart et al J. Chem. Soc. 85, 3260, (1963)] and N,N-dimethylformamide diethylacetal (6 ml) in a method analogous to that used in Example 1, to give the desired product as a yellow solid (2.26 g) m.p. 108–110°. MS (ES$^+$) 260 (MH$^+$, 100%).

EXAMPLE 16

6,6-Dimethyl-9-methoxy-N-[3-(2-pyrrolidinoethoxy) phenyl]benzo[h]-5,6-dihydroguinazoline-2-amine hydrochloride To a solution of 6,6-dimethyl-N-[3-(2-hydroxyethoxy) phenyl]-9-methoxybenzo[h]-5,6-dihydroquinazoline-2- amine (930 mg, 2.38 mmol) in dry pyridine (20 ml) was added 4-toluenesulphonyl chloride (1.81 g, 9.51 mmol) and the reaction was stirred at ambient temperature for 3 h. The mixture was poured into water (100 ml) and ethyl acetate (100 ml) and acidified with hydrochloric acid (2M). The layers were separated, the organic phase was washed with hydrochloric acid (2M), water and saturated aqueous $NaHCO_3$ and dried ($MgSO_4$). The solvent was removed under reduced pressure to give an off-white solid of which 366 mg was dissolved in dry DMF (8 ml). To this solution, pyrrolidine (0.55 ml, 6.70 mmol) was added and the resulting mixture was heated at 60° for 18 h. On cooling, the reaction was concentrated under reduced pressure and the residue partitioned between dichloromethane and aqueous $Na_2CO_3$. The organic phase was washed with brine, dried ($MgSO_4$) and concentrated under reduced pressure. The residue was purified by column chromatorgraphy (silica-gel; 8% methanol-dichloromethane). The purified material was dissolved in THF and treated with 1.0 M hydrogen chloride in diethyl ether (4 ml). The resulting solid was collected to give the title compound (251 mg) as a yellow solid m.p. 169–1730 8H ($d^6$ DMSO) 10.82 (1H, br s), 9.71 (1H, s), 8.40 (1H, s), 7.81 (1H, d, J 2.9 Hz), 7.70 (1H, t, J 2.24 Hz), 7.44 (1H, d, J 8.6 Hz), 7.41 (1H, m), 7.25 (1H, t, J 8.2 Hz), 7.11 (1H, dd, J 8.6, 2.9 Hz), 6.62 (1H, dd, J 8.0, 2.0 Hz), 4.37 (2H, t, J 4.8 Hz), 3.85 (3H, s), 3.58 (4H, m), 3.13 (2H, m), 2.72 (2H, s), 2.09–1.82 (4H, m) and 1.24 (6H, s).

The quinazoline-2-amine used as starting material in the above process was prepared by treating a solution of 6,6-dimethyl-N-(3-hydroxyphenyl)-9-methoxybenzo[h]-5,6-dihydroquinazoline-2-amine hydrochloride (1.32 g, 3.44 mmol) in dry DMF (25 ml) with $K_2CO_3$ (1.90 g) and ethylene carbonate (450 mg) at 100° for 18 h. After this time the solvent was removed under reduced pressure and the residue partitioned between $CH_2Cl_2$ (100 ml) and $H_2O$ (80 ml). The aqueous layer was reextracted with $CH_2Cl_2$ (2×50 ml) and the combined $CH_2Cl_2$ extracts washed with $H_2O$ (2×80 ml), brine (80 ml), dried ($MgSO_4$) and concentrated under reduced pressure. Chromatography on silica (40–60% ethyl acetate in hexane) gave the title compound as a light yellow solid (1.15 g) m.p. 130–131°. δH ($CDCl_3$) 8.25 (1H, s, 7.95 (1H, d, J 2.9HZ), 7.81 (1H, t, J 2.3 Hz), 7.34 (1H, d, J 8.5 Hz), 7.23 (1H, t, J 8.1 Hz), 7.19 (1H, br s), 7.06 (1H, ddd, J 8.1, 2.1 and 0.9 Hz), 7.01 (1H, dd, J 8.6, 2.9 Hz), 6.59 (1H, ddd, J 8.2, 2.5 and 0.9 Hz), 4.18 (2H, t, J 4.3 Hz), 4.00 (2H, m), 3.91 (3H, s), 2.71 (2H, s), 2,21 (1H, br s, OH) and 1.29 (6H, s).

The phenol used as starting material was prepared from 3-aminophenol (797 mg, 7.3 mmol) and 2-chloro-6,6-dimethyl-9-methoxybenzo[h]-5,6-dihydroquinazoline (2.0 g, 7.3 mmol) in a manner analogous to the corresponding material of Example 1 to give the desired material (1.65 g) as a yellow solid m.p. 217–223°.

2-Chloro-6,6-dimethyl-9-methoxybenzo[h]-5,6-dihydroquinazoline was prepared in a similar manner to the analogous starting material of Example 1, from 6,6-dimethyl-9-methoxybenzo[h]-5,6-dihydro-1 (H)-quinazolin-2-one and phosphorous oxychloride as a yellow solid m.p. 138°.

6,6-Methyl-9-methoxybenzo[h]-5,6-dihydro-1(H)-quinazolin-2-one was prepared as a buff solid m.p. >300° (decomp). 8H ($d^6$DMSO) 8.58 (1H, s), 7.56 (1H, d, J 2.6 Hz), 7.15 (1H, d, J 8.2 Hz), 6.87 (1H, dd, J 8.2, 2.6 Hz), 6.72 (1H, br s) and 2.85 (4H, m).

6,6-Dimethyl-9-methoxybenzo[h]-5,6-dihydroquinazoline-2-amine was prepared as a beige solid m.p. 188°. δH ($CDCl_3$) 8.14 (1H, s), 8.05 (1H, s), 7.18 (1H, dd, J 7.6, 1.3 Hz), 7.12 (1H, d, J 7.6 Hz), 4.98 (2H, br s), 2.89-2.85 (2H, m), 2.78–2.73 (2H, m) and 2.40 (3H, s).

The following compounds of Examples 17 and 18 were prepared in a similar manner to the compound of Example 16:

EXAMPLE 17

N-{3,5-Dichloro-4-[2-(4-methylpiperazin-1-yl)ethoxy]phenyl}-6,6-dimethyl-9-methoxybenzo[h]-5,6-dihydroquinazoline-2-amine hydrochloride From N-[3,5-dichloro-4-(2-hydroxyethoxy)phenyl]-6,6-dimethyl-9-methoxybenzo[h]-5,6-dihydroquinazoline-2-amine (700 mg, 1.52 mmol), 4-toluenesulphonyl chloride (584 mg, 3.04 mmol) and 1-methylpiperazine (780 mg, 7.82 mmol) to give the title compound (430 mg) as an off-white solid m.p. 136–138°. δH ($CDCl_3$) ($d^6$ DMSO) 10.40 (1H, br s), 9.88 (1H, s), 8.44 (1H, s), 8.08 (2H, s), 7.79 (1H, d, J 2.8 Hz), 7.43 (1H, d, J 8.6 Hz), 7.09 (1H, dd, J 8.6, 2.8 Hz), 4.10 (2H, m), 3.88 (3H, s), 3.39–2.60 (12H, m), 2.50 (3H, s) and 1.23 (6H, s).

N-[3,5-Dichloro-4-(2-hydroxyethoxy)phenyl]-6,6-dimethyl-9-methoxybenzo[h]-5,6-dihydroquinazoline-2-amine was prepared from N(3,5-dichloro-4-hydroxyphenyl)-6,6-dimethyl-9-methoxybenzo[h]-5,6-dihydroquinazoline-2-amine (1.50 g, 5.97 mmol) ethylene carbonate (450 mg) and potassium carbonate (1.82 g, 13.2 mmol), as for the analogous starting material of Example 16, to give a pale grey solid (800 mg) m.p. 134–137°. δH ($d^6$ DMSO) 9.84 (1H, s), 8.42 (1H, s), 8.03 (2H, s), 7.08 (1H, dd, J 8.6, 2.8 Hz), 4.84 (1H, t, J 5.7 Hz), 3.96 (2H, t, J 5.3 Hz), 3.87 (3H, s), 3.74 (2H, dt, J 5.7, 5.3 Hz), 2.72 (2H, s) and 1.23 (6H, s).

N-(3,5-Dichloro-4-hydroxyphenyl)-6,6-dimethyl-9-methoxybenzo[h]-5,6-dihydroquinazoline-2-amine was prepared from 2-chloro-6,6-dimethyl-9-methoxybenzo[h]-5,6-dihydroquinazoline (2.0 g, 7.28 mmol) and 2,6-dichloro-4-aminophenol (1.43 g, 8.01 mmol) as a yellow-brown solid (2.59 g) m.p. >250°. δH ($d^6$ DMSO) 9.83 (1H, s), 9.0 (2H, br s), 8.39 (1H, s), 7.91 (2H, s), 7.76 (1H, d, J 2.9 Hz), 7.42 (1H, d, J 8.6 Hz), 7.09 (1H, dd, J 8.6, 2.9 Hz), 3.86 (3H, s), 2.71 (2H, s) and 1.22 (6H, s).

EXAMPLE 18

6,6-Dimethyl-9-methoxy-N-[3-(2-pyrrodin-1-ylethyl)phenyllbenzo[h]-5,6-dihydroquinazoline-2-amine dihydrochloride From 6,6-dimethyl-N-[3-(2-hydroxyethyl)phenyl]-9-methoxybenzo[h]-5,6-dihydroquinazoline-2-amine (1.7 g, 4.5 mmol), 4-toluenesulphonyl chloride (3.5 g, 18.1 mmol) and pyrrolidine (2.1 ml, 25.6 mmol) to give the title compound (103 mg) as a yellow solid m.p. 248–250°. δH ($d^6$ DMSO) 11.1 (1H, br s), 9.86 (1H, s), 8.40 (1H, s), 7.77 (1H, d, J 2.8 Hz), 7.68 (2H, m), 7.43 (1H, d, J 8.6 Hz), 7.29 (1H, t, J 7.7 Hz), 7.11 (1H, dd, J 8.6, 2.9 Hz), 6.92 (1H, d, J 7.6 Hz), 3.83 (3H, s), 3.53 (2H, m), 3.34 (2H, m), 3.02 (4H, m), 2.71 (2H, s), 1.97 (4H, m) and 1.23 (6H, s).

6,6-Dimethyl-N-[3-(2-hydroxyethyl)phenyl]-9-methoxybenzo[h]-5,6-dihydroquinazoline-2-amine was prepared from 2-chloro-6,6-dimethyl-9-methoxybenzo[h]-5,6-dihydroquinazoline (2.0 g, 7.2 mmol) and 3-aminophenethyl alcohol (986 mg, 7.2 mmol) to give a yellow solid m.p. 202°. δH ($CDCl_3$) 10.71 (1H, br s), 8.09 (1H, s), 7.90 (1H, s), 7.63 (1H, s), 7.59 (1H, d, J 8.1 Hz), 7.40 (1H, d, J 8.7 Hz), 7.32 (1H, t, J 7.9 Hz), 7.16 (1H, dd, J 8.6, 2.8 Hz), 7.09 (1H, d, J 7.7 Hz), 3.92 (5H, m), 2.91 (2H, t, J 6.5 Hz), 2.76 (2H, s) and 1.31 (6H, s).

EXAMPLE 19

N-{[4,5-Dimethoxy-3-(2-pyrrolidin-1-ylethoxy]phenyl}-6,6-dimethylbenzo[h]-5,6-dihydroquinazoline-2-amine dihyrochloride salt From N-3,4-dimethoxy-5-hydroxyphenyl-6,6-dimethylbenzo[h]-5,6-dihydroquinazoline-2-amine (500 mg, 1.45 mmol), 1-(2-chloroethyl) pyrrolidine hydrochloride (371 mg, 2.18 mmol) and caesium carbonate (1.9 g, 5.8 mmol) to give the title compound (18 mg) as a yellow solid, m.p. >95°. δH (CDCl$_3$) 8.35 (1 h, d, J 8.2 Hz), 8.22 (1H, s), 7.42 (2H, m), 7.29 (2H, m), 7.15 (1H, d, J 2.3 Hz), 7.03 (1H, d, J 2.3 Hz), 4.31 (2H, t, J 5.7 Hz), 3.89 (3H, s), 3.80 (3H, s), 3.14 (2H, t, J 5.7 Hz), 2.91 (4H, m), 2.71 (2H, s), 1.89 (4H, m) and 1.30 (6H, s).

N-3,4-Dimethoxy-5-hydroxyphenyl-6,6-dimethylbenzo[h]-5,6-dihydroquinazoline-2-amine was prepared from 3,4-dimethoxy-5-hydroxyphenylguanidium nitrate (1.48 g, 5.4 mmol), 3,4-dihydro-4,4-dimethyl-2-dimethylaminomethylene-1(2H)-naphthalenone (1.24 g, 5.4 mmol) and sodium hydroxide (324 mg, 8.1 mmol) to give the desired compound (1.2 g) as a yellow solid m.p. 166°.

EXAMPLE 20

6,6-Dimethyl-9-methoxy-N-[3-(2-pyrrolidin-1-ylethoxy)-5-trifluoromethylphenyl]benzo[h]-5,6-dihydroquinazoline-2-amine dihydrochloride From 6,6-dimethyl-N-(3-hydroxy-5-trifluoromethylphenyl)-9-methoxybenzo [h]-5,6-dihydroquinazoline-2-amine (500 mg, 1.2 mmol), 1-(2-chloroethyl)pyrrolidine hydrochloride (210 mg, 1.2 mmol) and caesium carbonate (814 mg, 2.5 mmol) in a similar manner to the compound of Example 1 to give the title compound (33 mg) as a buff solid m.p. 206–208°. δH (d$^6$ DMSO) 11.14 (1H, br s), 10.03 (1H, s), 8.45 (1H, s), 8.04 (1H, s), 7.78 (2H, s), 7.43 (1H, d, J 8.7 Hz), 7.10 (1H, d, J 8.7 Hz), 6.91 (1H, s), 4.46 (2H, m), 3.84 (3H, s), 3.50 (4H, m), 3.11 (2H, m), 2.72 (2H, s), 2.01–1.90 (4H, m) and 1.23 (6H, s).

6,6-Dimethyl-N-(3-hydroxy-5-trifluoromethylphenyl)-9-methoxybenzo[h]-5,6-dihydroquinazoline-2-amine was prepared from 2-chloro-6,6-dimethyl-9-methoxybenzo[h]-5,6-dihydroquinazoline (2.0 g, 7.3 mmol) and 3-amino-5-trifluoromethylphenol (1.3 g, 7.3 mmol) to give a yellow solid (1.99 g) m.p. 178°. δH (d°DMSO) 9.91 (1H, s), 8.41 (1H, s), 7.81 (1H, s), 7.77 (1H, d, J 2.9 Hz), 7.51 (1H, s), 7.41 (1H, d, J 8.6 Hz), 7.08 (1H, dd, J 8.6, 2.9 Hz), 6.65 (1H, s), 5.79 (1H, br s), 3.82 (3H, s), 2.71 (2H, s) and 1.22 (6H, s).

EXAMPLE 21

6,6-Dimethyl-9-methoxy-N-[4-N-(2-pyrrolidin-1-yl) ethylsulphonamidophenyl]benzo[h]-5,6-dihydroquinazoline-2-amine A suspension of 2-chloro-6,6-dimethyl-9-methoxybenzo[h]-5,6-dihydroquinazoline (0.81 g, 2.93 mmol) and 4-amino-N-[2-pyrrolidin-1-ylethyl]benzenesulphonamide (0.79 g, 2.93 mmol) was heated at 200° in ethylene glycol (20 ml) containing 1.0 M hydrogen chloride in diethyl ether (2.93 ml). The reaction was partitioned between ethyl acetate and water. The organic layer was washed with brine, dried (MgSO$_4$) and evaporated under reduced pressure. The resulting residue was purified by column chromatography [silica gel; 10% methanol-dichloromethane] and crystallised from ethanol to give the title compound (310 mg) as a colourless solid m.p. 157°. δH (CDCl$_3$) 8.31 (1H, s), 7.89 (3H, m), 7.84 (2H, d, J 9.1 Hz), 7.46 (1H, brs), 7.35 (1H, d, J 8.6 Hz), 7.04 (1H, dd, J 8.6, 2.9 Hz), 3.92 (3H, s), 3.01 (2H, m), 2.74 *2H, s), 2.53 (2H, m), 2.35 (4H, m), 1.70 (4H, m) and 1.30 (6H, s).

The aniline used in the above process was prepared by treating a solution of 4-nitro-N-[(2-pyrrolidin-1-yl)ethyl] benzenesulphonamide (1.54 g, 5.15 mmol) in ethanol (60 ml) with tin (II) chloride at reflux temperature for 3 h. On cooling 2M NaOH was added to the reaction to give pH 11, and the resulting white precipitate was extracted with ethyl acetate. The organic washings were dried (MgSO$_4$) and concentrated under reduced pressure to give the desired product as a light brown oil. δH (CDCl$_3$) 7.58 (2H, d, J 9.4 Hz), 6.63 (2H, d, J 9.4 Hz), 4.19 (2H, br s), 2.92 (2H, t, J 6.7 Hz), 2.47 (2H, t, J 6.5 Hz), 2.33 (4H, m) and 1.66 (4H, m).

The sulphonamide was prepared by treating a solution of 4-nitrobenzenesulphonyl chloride (2.0 g, 9.0 mmol) in dichloromethane (25 ml) with 1-(2-aminoethyl)pyrrolidine (1.03 g, 9. mmol) and triethylamine (1.42 ml, 10 mmol) at room temperature for 12 h. The reaction was washed with water, dried (MgSO$_4$) and concentrated under reduced pressure. The residue crystallised from ether to give the desired product as a beige solid (2.37 g) m.p. 98°. δH (CDCl$_3$) 8.36 (2H, d, J 8.9 Hz), 8.08 (2H, d, J 8.9 Hz), 3.16 (2H, t, J 5.6 Hz), 2.76 (2H, t, J 5.6 Hz), 2.65 (4H, m) and 1.84 (4H, m).

EXAMPLE 22

6,6-Dimethyl-9-methoxy-N-(3-pyrrolidin-1-ylcarbonylphenyl)benzo[h]-5,6-dihydroquinazoline-2-amine hydrochloride A solution of N-(3-carboxyphenyl)-6,6-dimethyl-9-methoxybenzo[h]-5,6-dihydroquinazoline-2-amine hydrochloride (1.0 g, 2.43 mmol) and pyrrolidine (190 mg, 2.68 mmol) in dry DMF (5 ml) was treated with N-methylmorpholine (0.98 g, 9.72 mmol), EDC (0.51 g, 2.67 mmol) and HOBt (0.36 g, 2.67 mmol) at ambient temperature for 12 h. The reaction was partitioned between saturated aqueous NaHCO$_3$ and ethyl acetate. The organic phase was washed with 2MHCl (2×25 ml), and brine (1×25 ml), dried (MgSO$_4$) and concentrated under reduced pressure. The residue was crystallised form dichloromethane-hexane to give the title compound (170 mg) as a yellow solid m.p. 203–206°. δH (d$^6$ DMSO) 9.80 (1H, s), 8.41 (1H, s), 8.20 (1H, s), 7.78 (2H, m), 7.42 (1H, d, J 8.6 Hz), 7.35 (1H, t, J 7.8 Hz), 7.08 (2H, m), 3.83 (3H, s), 3.47 (2H, t, J 6.6 Hz), 3.40 (2H, t, J 6.6 Hz), 2.72 (2H, s), 1.85 (4H, m) and 1.24 (6H, s).

N-(3-Carboxyphenyl)-6,6-dimethyl-9-methoxybenzo[h]-5,6-dihydroquinazoline-2-amine hydrochloride was prepared from 2-chloro-6,6-dimethyl-9-methoxybenzo[h]-5,6-dihydroquinazoline and 3-aminobenzoic acid to give the title compound as a yellow solid, m.p. >300°. δH (d$^6$ DMSO) 10.01 91H, s), 8.60 (1H, t, J 1.8 Hz), 8.42 (1H, s), 7.91 (1H, m), 7.82 (1H, d, J 2.8 Hz), 7.56 (1H, m), 7.42 (2H, m), 7.08 (1H, dd, J 8.6, 2.9 Hz), 3.82 (3H, s), 2.71 (2H, s) and 1.22 (6H, s).

EXAMPLE 23

N-[3,4-Dimethoxy-5-(2-pyrrolidin-1-yl)ethoxy]phenyl-6,6,9-trimethylbenzofh]-5,6-dihydroquinazoline-2-amine dihydrochloride From N-[3,4-dimethoxy-5-(2-hydroxyethoxy)phenyl]-6,6,9-trimethylbenzo [h]-5,6-dihydroquinazoline-2-amine (350 mg, 0.73 mmol), 4-toluenesulphonyl chloride (420 mg, 2.21 mmol) and pyrrolidine in a manner analogous to Example 16, to give the title compound (98 mg) as a yellow solid m.p. 188°. δH (d$^6$ DMSO) 9.65 (1H, s), 8.36 (1H, s), 8.11 (1H s), 7.52 (1H, s), 7.39 (1H, d, J 8.0 Hz), 7.34 (1H, d, J 8.0 Hz), 7.14 (1H, s), 4.37 (2H, m), 3.86 (3H, s), 3.61 (4H, m), 3.15 (2H, m), 2.71 (2H, m), 2.34 (3H, m), 2.02–1.89 (4H, m) and 1.23 (6H, s).

N-[3,4-Dimethoxy-5-(2-hydroxyethoxy)phenyl]-6,6,9-trimethylbenzo[h]-5,6-dihydroquinazoline-2-amine was prepared from N-(3,4-dimethoxy-5-hydroxyphenyl)-6,6,9-trimethylbenzo[h]-5,6-dihydroquinazoline-2-amine (390 mg, 0.99 mmol), ethylene carbonate (132 mg, 1.5 mmol) and potassium carbonate (138 mg, 1.0 mmol) to give a yellow solid (273 mg) m.p. 112°. δH (CDCl$_3$) 8.21 (2H, s), 7.41 (1H, s), 7.35–7.29 (2H, m), 7.21 (1H, d, J 2.4 Hz), 7.09 (1H, d, J 2.4 Hz), 4.22 (2H, t, J 4.3 Hz), 3.95 (3H, s), 3.94 (2H, t, J 4.3 Hz), 3.86 (3H, s), 2.71 (2H, s), 2.39 (3H, s) and 1.30 (6H, s).

The phenol starting material was prepared from 3,4-dihydro-4,4,7-trimethyl-2-dimethylaminomethylene-1-(2H) naphthalenone (0.42 g, 1.82 mmol) and $^{3,4}$-dimethoxy-5-hydroxyphenylguanidinium nitrate (0.5 g, 1.82 mmol) heated at reflux in 2-ethoxyethanol (10 ml) in the presence of potassium carbonate (280 mg, 2.0 mmol). The solvent was removed under reduced pressure and the residue partitioned between ethyl acetate and water. The organic phase was dried (MgSO$_4$), concentrated under reduced pressure and purified by column chromatography [silica gel; 40% ethyl acetate/hexane] to give the desired material as a yellow solid. 8H (CDCl$_3$) 8.24 (1H, s), 8.22 (1H, m), 7.40 (1H, m), 7.34–7.26 (2H, m), 6.77 (1H, d, J 2.5 Hz), 3.98 (3H, s), 3.89 (3H, s), 2.70 (2H, s), 2.39 (3H, s) and 1.29 (6H, s).

The naphthalenone was prepared from 4,4,7-trimethyl-1-tetralone (4.99 g, 26.5 mmol) and dimethylformamide diethylacetal (13.6 ml, 79.5 mmol) in a similar manner to the analogous starting material of Example 1 as a yellow solid (2.65 g), m.p. 121°. δH (CDCl$_3$) 7.86 (1 h, m), 7.76 (1H, s), 7.27–7.18 (2H, m), 3.12 (6H, s), 2.77 (2H, s), 2.35 (3H, s) and 1.30 (6H, s).

The tetralone used above was prepared by heating 4-methyl-4-tolylpentanoic acid (10 g, 48.5 mmol) in polyphosphoric acid at 900, for 15 min. The reaction was poured onto 250 g of ice-water and the resulting brown gum was stirred until a buff precipitate was obtained. The suspension was extracted with ethyl acetate (2×150 ml), the combined organic washings dried (MgSO$_4$) and concentrated under reduced pressure to a residue which was subjected to column chromatography [silica gel; 30% ethyl acetate-hexane] to give the desired material as a clear oil (5.02 g). δH (CDCl$_3$) 7.82 (1H, m), 7.32 (2H, m), 2.70 (2H, m), 2.34 (3H, s), 2.02 (2H, m) and 1.36 (6H, s).

EXAMPLE 24

9-Bromo-N-[4-(2-piperidin-1-ylethyl)phenyl]-6,6-dimethylbenzo[h]-5,6-dihydroquinazoline-2-amine From 9-bromo-6,6-dimethyl-N-(4-hydroxyethylphenyl) benzo[h]-5,6-dihydroquinazoline-2-amine (7.0 g, 16.5 mmol), 4-toluenesulphonyl chloride (4.72 g, 24.8 mmol) and piperidine (5.13 ml, 51.9 mmol) to give the title compound (1.80 g) as a yellow solid (1.8 g, 77%) m.p. 152–1540 in a manner similar to Example 16. δH (CDCl$_3$) 8.45 (1H, d, J 2.2 Hz), 8.24 (1H, s), 7.60 (2H, d, J 8.5 Hz), 7.55 (1H, dd, J 8.3, 2.3 Hz), 7.28 (1H, d, J 8.3 Hz), 7.21 (2H, d, J 8.5 Hz), 7.11 (1H, br s), 2.89 (2H, m), 2.71 (2H, s), 2.70–2.51 (6H, m), 1.70 (4H, m), 1.50 (2H, m) and 1.29 (6H, s).

9-Bromo-6,6-dimethyl-N-(4-hydroxyethylphenyl)benzo [h]-5,6-dihydroquinazoline-2-amine was prepared from 7-bromo-3,4-dihydro-4,4-dimethyl-2-dimethylaminomethylene-1(2H)naphthalenone (9.24 g, 30 mmol) 4-hydroxyethylphenylguanidinium nitrate (8.71 g, 36.0 mmol) and sodium hydroxide (1.58 g, 39.6 mmol) to give the desired compound as a yellow solid m.p. 151°. δH (CDCl$_3$) 8.45 (1H, d, J 2.3 Hz), 8.24 (1H, s), 7.63 (2H, dt, J 8.5, 2.0 Hz), 7.56 (1H, dd, J 8.3, 2.2 Hz), 7.29 (1H, d, J 8.3 Hz), 7.26 (1H, br s), 7.26 (1H, br s), 7.24 (2H, m, J 8.5 Hz), 3.87 (2H, t, J 6.5 Hz), 2.87 (2H, t, J 6.5 Hz), 2.71 (2H, s) and 1.29 (6H, s).

EXAMPLE 25

6,6-Dimethyl-9-(2-furyl)-N-[4-(2-piperdin-1-ylethyl) phenyl]benzo[h]-5,6-dihydroquinazoline-2-amine To a solution of the compound of Example 24 (491 mg, 1.0 mmol) in dimethoxyethane (15 ml) at ambient temperature was added tetrakis(triphenylphosphine) palladium (O) (130 mg, 0.1 mmol). After 5 min. 2.0 M Na$_2$CO$_3$ (1.1 ml) was added, followed by 2-furylboronic acid (116 mg, 1.1 mmol) and the mixture was then heated at reflux for 12 h. On cooling the reaction was partitioned between ethyl acetate (80 ml) and water (20 ml). The organic phase was dried (MgSO$_4$) and concentrated under reduced pressue to give a residue which was subjected to column chromatography (silica gel, 10% methanol-dichloromethane) giving the title compound (390 mg) as a yellow solid m.p. 139–141°. δH (CDCl$_3$) 8.65 (1H, d, J 2.0 Hz), 8.25 (1H, s), 7.76 (1H, dd, J 8.2, 2.0 Hz), 7.67 (2H, d, J 8.5 Hz), 7.52 (1H, dd, J 1.1, <1.0 Hz), 7.44 (1H, d, J 8.2 Hz), 7.22 (2H, d, J 8.5 Hz), 7.11 (1H, br s), 6.74 (1H, dd, J 3.3, <1.0 Hz), 6.52 (1H, dd, J 3.3, 1.8 Hz), 2.90 (2H, m), 2.73 (2H, s), 2.73–2.51 (6H, m), 1.72 (4H, br m), 1.50 (2H, br m) and 1.32 (6H, s).

EXAMPLE 26

9-(N,N-Dimethylcarboxamido)-6,6-dimethyl-N-[4-(2-pyrrolidinoethylphenyl)]benzo[h]-5,6-dihydroquinazoline-2-amine From 9-(N,N-dimethylcarboxamido)-6,6-dimethyl-N-[4-(2-hydroxyethylphenyl)]benzo[h]-5,6-dihydroquinazoline-2-amine (810 mg, 1.95 mmol), 4-toluenesulphonyl chloride (559 mg, 2.93 mmol) and pyrrolidine (0.33 ml, 3.9 mmol) in a manner similar to the preparation of the compound of Example 16 to give the title compound (117 mg) as a yellow solid m.p. 129°. δH (CDCl$_3$) 8.38 (1H, d, J 1.8 Hz), 8.24 (1H, s), 7.62 (2H, d, J 8.5 Hz), 7.54 (1H, dd, J 8.0, 1.9 Hz), 7.45 (1H, d, J 8.0 Hz), 7.19 (2H, d, J 8.5 Hz), 7.16 (1H, br s), 3.11 (6H, br d), 3.01–2.97 (8H, m), 2.72 (2H, s), 1.93 (4H, m) and 1.31 (6H, s).

The alcohol used as starting material in the above process was prepared in a similar manner to the compound of Example 22 from 9-carboxy-6,6-dimethyl-N-[4-(2-hydroxyethylphenyl)]benzo[h]-5,6-dihydroquinazoline-2-amine (1.0 g, 2.57 mmol), EDC (543 mg, 2.83 mmol), dimethylamine hydrochloride (1.05 g, 12.85 mmol), N-methylmorpholine (2.3 ml, 20.6 mmol) and HOBt (385 mg, 2.83 mmol) to give the desired material (890 mg) as a yellow solid m.p. °. δH (d$^6$ DMSO) 9.46 (1H, s), 8.37 (1H, s), 8.30 (1H, t, J 1.1 Hz), 7.71 (2H, d, J 8.5 Hz), 7.56 (2H, d, J 1.1 Hz), 7.12 (2H, d, J 8.5 Hz), 4.59 (1H, t, J 5.2 Hz), 3.57 (2H, m), 3.01 (6H, br s), 2.75 (2H, s), 2.68 (2H, t, J 7.2 Hz) and 1.28 (6H, s).

The carboxylic acid used in the above process was prepared by treatment of 6,6-dimethyl-N-[4-(2-hydroxyethylphenyl)]-9-methoxycarbonyl benzo[h]-5,6- dihydroquinazoline-2-amine (1.05 g) with lithium hydroxide monohydrate (240 mg, 5.74 mmol) in THF (24 ml) and water (6 ml) at reflux temperature for 12 h. On cooling the reaction was diluted with 2M hydrochloric acid (10 ml) and the resulting precipitate collected and dried to give the desired material (833 mg) as a yellow powder. δH (d$^6$ DMSO) 9.52 (1H, s), 8.91 (1H, d, J 1.9 Hz), 8.38 (1H, s), 8.05 (1H, dd, J 8.1, 1.9 Hz), 7.73 (2H, d, J 8.5 Hz), 7.63 (1H, d, J 8.1 Hz), 7.12 (2H, d, J 8.5 Hz), 3.58 (2H, t, J 7.2 Hz), 2.76 (2H, s), 2.68 (2H, t, J 7.2 Hz) and 1.29 (6H, s).

The ester described above was prepared by treatment of 9-bromo-6,6-dimethyl-N-(4-hydroxyethylphenyl)benzo[h]-5,6-dihydroquinazoline-2-amine (Example 24) (1.54 g, 3.63 mmol) dissolved in methanol (5 ml) and DMF (10 ml) saturated with carbon monoxide, with palladium (II) acetate (41 mg, 0.1 8 mmol), 1,3-bis(diphenylphosphino)propane (75 mg, 0.18 mmol) and triethylamine (1.01 ml, 7.26 mmol) at 70° under an atmosphere of carbon monoxide. On cooling the excess carbon monoxide was dissipated and the solvent removed under reduced pressure. The resulting residue was purified by column chromatography [silica gel 50%; ethyl acetate-hexane] to give the product (1.06 g) as a yellow solid, m.p. 164–165°. δH (CDCl$_3$) 8.99 (1H, d, J 1.9 Hz), 8.23 (1H, s), 8.13 (1H, dd, J 8.1,1.9 Hz), 7.68 (2H, m), 7.57 (1H, br s), 7.51 (1H, d, J 8.1 Hz), 7.25 (2H, m), 3.97 (3H, s), 3.87 (2H, t, J 6.5 Hz), 2.87 (2H, t, J 6.5 Hz), 2.76 (2H, s) and 1.33 (6H, s).

EXAMPLE 27

6,6-Dimethyl-9-methoxy-N-[3-(pyrrolidin-1-ylmethyl) phenyl]benzo[h]-5,6-dihydroquinazoline-2-amine dihydrochloride 6,6-Dimethyl-N-[3-(hydroxymethyl)phenyl]-9-methoxybenzo[h]-5,6-dihydroquinazoline-2-amine (800 mg, 2.01 mmol) was suspended in chloroform (50 ml) containing thionyl chloride (0.44 ml, 6 mmol) and heated at reflux for 0.5 h. The mixture was then washed with 2M NaOH, the organic phase dried (MgSO$_4$) and concentrated under reduced pressure. The resulting residue was dissolved in acetonitrile (25 ml) to which pyrrolidine (0.84 ml, 10 mmol) was added and the resulting solution heated at reflux for 0.75 h. On cooling the solvent was removed under reduced pressure and the residue purified by column chromatography (silica gel: 10% methanol-dichloromethane) to give the product, which was then dissolved in dichloromethane and treated with 1.0M hydrogen chloride in diethyl ether (2.5 ml) to give the title compound (515 mg) as a yellow solid m.p. 135–136°. δH (d$^6$ DMSO) 11.12 (1H, br s), 9.81 (1H, s), 8.40 (1H, s), 7.94 (1H, s), 7.86–7.79 (2H, m), 7.43–7.29 (3H, s), 7.10 (1H, dd, J 8.6, 2.9 Hz), 6.35 (1H, br s), 4.30 (1H, d, J 5.7 Hz), 3.84 (3H, s), 3.41–3.30 (2H, m), 3.10–3.05 (2H, m), 2.72 (2H, s), 2.03–1.90 (4H, m) and 1.23 (6H, s).

The starting material in the above process was prepared from 2-chloro-6,6-dimethylbenzo[h]-5,6-dihydroquinazoline (750 mg, 2.73 mmol) and 3-aminobenzyl alcohol (337 mg, 2.73 mmol) to give the desired product (815 mg) as a yellow solid m.p. 175–177°. δH (d$^6$ DMSO) 10.04 (1H, br s), 8.42 (1H, s), 7.84 (1H, s), 7.80 (1H, d, J 5.2 Hz), 7.62–7.59 (1H, m), 7.43 (1H, d, J 8.6 Hz), 7.29 (1H, t, J 8.7 Hz), 7.12 (1H, dd, J 8.6, 2.5 Hz), 6.98 (1H, d, J 7.5 Hz), 4.51 (2H, s), 3.85 (3H, s), 2.75 (2H, s) and 1.24 (6H, s).

EXAMPLE 28

6,6-Dimethyl-9-nitro-N-[4-(pyrrolidinyl-3(S)-oxy) phenyl]benzo[h]-5,6-dihydroquinazoline-2-amine From 2-chloro-6,6-dimethyl-9-nitrobenzo[h]-5,6-dihydroquinazoline (1.0 g, 3.45 mmol) and 3(S)-(4-aminophenoxy)pyrrolidine (741 mg, 3.45 mmol) in ethyleneglycol (2 ml) in a similar manner to the preparation of the compound of Example 9 to give the title compound (750 mg) as an orange solid m.p. 142–143°. δH (d$^6$ DMSO) 9.49 (1H, s), 9.01 (1H, d, J 5.2 Hz), 8.40 (1H, s), 8.31 (1H, dd, J 8.6, 2.6 Hz), 7.78 (1H, d, J 8.6 Hz), 7.67 (2H, d, J 9.0 Hz), 6.86 (2H, d, J 9.0 Hz), 4.82–4.78 (1H, m), 3.27 (3H, br s), 3.04 (1H, dd, J 12.1 Hz, 5.3 Hz), 2.96–2.73 (3H, m), 2.78 (2H, s), 2.03–1.94 (1H, m), 1.79–1.76 (1H, m) and 1.30 (6H, s).

The chloropyrimidine used as starting material was prepared in a similar manner to the analogous starting material of Example 1, from 6,6-dimethyl-9-nitrobenzo[h]-5,6-dihydro-1(H)-quinazoline-2-one trifluoro-acetate and phosphorous oxychloride as a yellow solid. δH (d$^6$ DMSO) 8.86 (1H, s), 8.75 (1H, s), 8.37 (1H, d, J 8.5 Hz), 7.83 (1H, d, J 8.5 Hz), 2.95 (2H, s) and 1.31 (6H, s).

The quinazoline-2-one was prepared by treating 6,6-dimethyl-9-nitrobenzo[h]-5,6-dihydroquinazoline-2-amine (5.0 g, 18.1 mmol) in trifluoroacetic acid (100 ml) and water (20 ml) with sodium nitrite solution (3.73 g in 80 ml of water) in a dropwise manner at room temperature. After 1 h a yellow precipitate was formed. This was collected and dried to give the quinazoline-2-one trifluoroacetate (4.01 g) as a yellow solid m.p. °. δH (d$^6$ DMSO) 8.89 (1H, d, J 2.6HZ), 8.34 (1H, dd, J 8.7, 2.6 Hz), 7.97 (1H, s), 7.79 (1H, d, J 8.7 Hz), 2.67 (2H, s) and 1.29 (6H, s). 6,6-Dimethyl-9-nitrobenzo[h]-5,6-dihydroquinazoline-2-amine was prepared from 3,4-dihydro-2-dimethylaminomethylene-7-nitro-1 (2H)-naphthalenone (11.0 g, 40.1 mmol) guanidine hydrochloride (3.92 g, 41 mmol) and sodium hydroxide (1.64 g, 41 mmol) as a yellow solid (12.01 g) m.p. 270°. δH (d$^6$ DMSO) 8.93 (1H, d, J 2.6 Hz), 8.27 (1H, dd, J 8.6, 2.6 Hz), 8.21 (1H, s), 7.73 (1H, d, J 8.6 Hz), 6.66 (2H, br s), 2.69 (2H, s) and 1.27 (6H, s).

The naphthalenone used in the above process was prepared from 4,4-dimethyl-7-nitro-1-tetralone (Kleinm E, et al, International Patent Specification No. WO 97/09297) (1.06 g, 4.57 mmol) and N,N-dimethylformamide diethylacetal (3.5 ml) using a method analogous to that used for the naphthalenone starting material of Example 1, giving a yellow solid m.p. 123–125°.

EXAMPLE 29

9-Acetamido-6,6-dimethyl-N-{4-[3(S)-pyrrolidinyloxy] phenyl}benzo[h]-5,6-dihydroquinazoline-2-amine bistrifluoroacetate 9-Acetamido-N-{4-[3(S) (1-t-butoxycarbonyl) pyrrolidinyloxy]phenyl}-6,6-dimethylbenzo[h]-5,6-dihydroquinazoline-2-amine (200 mg, 0.37 mmol) was dissolved in ethyl acetate (40 ml) and 1 M hydrogen chloride in diethyl ether (1.5 ml) was added, the resulting solution then being stirred for 3 h at room temperature. The solvent was removed under reduced pressure and the residue purified by HPLC [dynamax C18 column, isocratic run, 75% of 0.2% trifluoroacetic acid in water/acetonitrile], to give the title compound as a yellow solid m.p. >300°. δH (d$^6$ DMSO) 10.06 (1H, s), 9.42 (1H, s), 9.10 (2H, brs), 8.69 (1H, s), 8.34 (1H, s), 7.86 (2H, d, J 9.0 Hz), 7.58–7.53 (1H, m), 7.42–7.39 (1H, m), 6.98 (2H, d, J 9.0 Hz), 5.08–5.06 (1H, m), 3.45-3.30 (4H, br m), 2.70 (2H, s), 2.22–2.17 (2H, m), 2.11 (3H, s) and 1.24 (6H, s).

The starting material for the above process was prepared by treating 9-amino-N-{4-[3(S)-(1-t-butoxycarbonyl) pyrrolidinyloxy]phenyl}-6,6-dimethylbenzo[h]-5,6- dihydroquinazoline-2-amine (450 mg, 0.89 mmol) in toluene (30 ml) with acetic anhydride (0.4 ml, 4.2 mmol), pyridine (0.5 ml) and dimethylaminopyridine (10 mg) at reflux temperature for 1.5 h. On cooling the solvent was removed under reduced pressure, and the residue purified by column chromatography [silica gel; 75% ethyl acetate-hexane] to give the desired product as a yellow foam. δH (CDCl$_3$) 8.35–8.25 (1H, m), 8.19 (1H, s), 7.80–7.55 (4H, m), 7.37 (1H, d, J 8.6 Hz), 7.17 (1H, brs), 6.88 (2H, d, J 9.0 Hz), 4.88–4.84 (1H, m), 3.65–3.50 (4H, m), 2.67 (2H, s), 2.21 (3H, s), 2.10–2.05 (2H, s), 1.48 (9H, s) and 1.27 (6H, s).

The quinazoline used above was prepared from N-{4-[3 (S)-(1-tert-butoxycarbonyl)pyrrolidinyloxy]phenyl}-6,6-dimethyl-9-nitrobenzo[h]-5,6-dihydroquinazoline-2-amine (850 mg), 10% palladium on carbon (200 mg) and ammonium formate (2.0 g) as a yellow solid (450 mg). δH (CDCl$_3$) 8.27–8.15 (2H, m), 7.70–7.51 (4H, m), 7.35 (1H, d, J 8.6 Hz), 7.17 (1H, br s), 6.88 (2H, d, J 9.0 Hz), 4.87–4.83 (1H, m), 3.70–3.55 (4H, m), 2.65 (2H, s), 2.10–2.05 (2H, m), 1.48 (9H, s) and 1.30 (6H, s).

The above starting material was prepared by suspending the compound of Example 28 (0.7 g, 1.62 mmol) in dichloromethane (50 ml) and treating with di-tert-butyl dicarbonate (354 mg, 1.62 mmol) and triethylamine (226 μl, 1.6 mmol) at ambient temperature for 2 h. The reaction was washed with saturated NaHCO$_3$, then the organic phase was dried (MgSO$_4$) and concentrated under reduced pressure to give the desired product (862 mg) as a yellow solid. δH (CDCl$_3$) 9.14 (1H, d, J 2.6 Hz), 8.28 (1H, s), 8.26 (1H, dd, J 8.6, 2.6 Hz), 7.60–7.56 (3H, m), 7.11 (1H, br s), 6.91 (2H, d, J 9.0 Hz), 4.89–4.87 (1H, m), 3.64–3.58 (4H, m), 2.77 (2H, s), 2.18–2.09 (2H, m), 1.47 (9H, s) and 1.35 (6H, s).

EXAMPLE 30

9-Methoxy-N-[4-(4-methylpiperazin-1-yl)phenyl]benzo[h]-5,6-dihydroquinazoline-2-amine hydrochloride A mixture of [4-(4-methylpiperazin-1-yl)phenyl]guanidine nitrate (3.74 g, 10.56 mmol), 3.4-dihydro-2-(dimethylaminomethylene)-6-methoxy-1 (2H)-naphthalenone (2.46 g, 10.65 mmol) and potassium carbonate (4.56 g, 33.04 mmol) was heated at reflux in 2-ethoxyethanol (30 ml) for 12 h under an atmosphere of nitgoren. On cooling the solvent was removed under reduced pressure and the residue partitioned between ethyl acetate and water. The organic phase was dried (MgSO$_4$) and evaporated to a residue, which was subjected to column chromatography (silica, 10% methanol-dichloromethane). The material so obtained was dissolved in ethyl acetate which was then saturated with hydrochloric acid gas to give the title compound (145 mg) as a yellow solid m.p. >240°. δH (CDCl$_3$) 8.23 (1H, s), 7.84 (1H, d, J 2.8 Hz), 7.58 (2H, d, J 8.9 Hz), 7.15 (1H, d, J 8.3 Hz), 6.99–6.93 (4H, m), 3.89 (3H, s), 3.19 (4H, m), 2.88–2.77 (4H, m), 2.63 (4H, m) and 2.38 (3H, s), MS (ES+) 402 (MH$^+$).

The following compound was prepared in a similar manner:

EXAMPLE 31

6,6-Dimethyl-9-methoxy-N-[4-(4-methylpiperazin-1-yl)phenyl]-benzo[h]-5,6-dihydroquinazoline-2-amine From 3,4-dihydro-4,4-dimethyl-2-(dimethylaminomethylene)-7-methoxy-1(2H)-naphthalenone (1.0 g, 3.86 g), [4-(4-methylpiperazin-1-yl)phenylguanidine nitrate (1.73 g, 3.86 mmol) and potassium carbonate (1.20 g, 12 mmol) to give the title compound (41 mg) as a yellow soid m.p. 125–127°. δH (CDCl$_3$) 8.19 (1H, s), 7.89 (1H, d, J 2.9 Hz), 7.57 (2H, d, J 8.9 Hz), 7.32 (1H, d, J 8.6 Hz), 7.02–6.94 (4H, m), 3.89 (3H, s), 3.19–3.16 (4H, m), 2.68 (2H, s), 2.61–2.58 (4H, m), 2.36 (3H, s) and 1.28 (6H, s). MS(ES$^+$) 430 (MH$^+$).

EXAMPLE 32

6,6-Dimethyl-9-methoxy-N-[3-(4-methylpiperazin-1-yl)phenyl]benzo[h]-5,6-dihydroquinazoline-2-amine hydrochloride A mixture of 2-chloro-6,6-dimethyl-9-methoxybenzo[h]-5,6-dihydroquinazoline (0.6 g, 2.2 mmol) and 3-(4-methylpiperazin-1-yl)aniline 9450 mg, 2.2 mmol) in ethylene glycol (5 ml) was treated with 1 M hydrochloric acid in diethyl ether (2.2 ml) and heated at 200° for 12 h. The reaction was partitioned between saturated sodium carbonate and ethyl acetate., the organic phase washed with brine, dried (MgSO$_4$) and evaporated under reduced pressure. The residue was subjected to column chromatography (silica gel, 10% methanol-dichloromethane) and the material obtained was taken up in ethyl acetate saturated with hydrochloric acid gas to give the title compound (110 mg) as an orange solid m.p. 110°. δH (d$^6$DMSO) 9.64 (1H, br s), 8.38 (1H, s), 7.78 (1H, br s), 7.61 (1H, s), 7.31 (1H, d, J 8.8 Hz), 7.19 (1H, m), 7.11 (1H, dd, J 8.6, 2.8 Hz), 6.64 (1H, d, J 7.1 Hz), 3.83 (3H, s), 3.78–3.75 (2H, m), 3.47 (2H, brs), 3.17–3.14 (4H, m), 2.81 (3H, s), 2.71 (1H, s) and 1.23 (6H, s). MS (ES+) 430 (MH+).

The following compounds of Examples 33–36 were prepared in a similar manner as the free base:

EXAMPLE 33

6,6-Dimethyl-9-methoxy-N-[4-(3-methylpiperazin-1-yl)phenyl]benzo[h]-5,6-dihydroquinazoline-2-amine From 2-chloro-6,6-dimethyl-9-methoxybenzo[h]-5,6-dihydroquinazoline (1.0 g, 3.6 mmol) and 4-(3-methylpiperazin-1-yl)aniline (0.78 g, 3.6 mmol) to give the title compound (0.59 g) as a buff solid m.p. 106°. δH (CDCl$_3$) 8.20 (1H, s), 7.90 (1H, d, J 2.9 Hz), 7.58 (2H, d, J 9.0 Hz), 7.32 (1H, d, J 5.8 Hz), 7.02–6.93 (4H, m), 3.89 (3H, s), 3.47–3.43 (2H, m), 3.10–3.01 (3H, m), 2.72–2.65 (1H, m), 2.68 (2H, s), 2.37–2.29 (1H, m), 1.28 (6H, s) and 1.13 (3H, d, J 6.3 Hz).

EXAMPLE 34

6,6-Dimethyl-9-methoxy-N-[4-(4-methyl-1 4-perhydrodiazepin-1-yl)phenyl]benzo[h]-5,6-dihydroquinazoline-2-amine From 2-chloro-6,6-dimethyl-9-methoxybenzo[h]-5,6-dihydroquinazoline (0.41 g, 1.5 mmol) and 4-(4-methyl-1,4-perhydrodiazepin-1-yl)aniline (0.31 g, 1.5 mmol) to give the title compound (341 mg) as a gold solid m.p. 104°. δH (CDCl$_3$) 8.18 (1H, s), 7.89 (1H, d, J 2.9 Hz), 7.48 (2H, d, J 9.0 Hz), 7.32 (1H, d, J 8.6 Hz), 6.99 (1H, d, J 6.5 Hz), 6.83 (1H, br s), 6.71 (2H, d, J 9.0 Hz), 3.90 (3H, s), 3.58–3.56 (2H, m), 3.51–3.47 (2H, m), 2.72 (2H, m), 2.68 (2H, s), 2.56 (2H, m), 2.39 (3H, s), 2.02 (2H, m) and 1.28 (6H, s). MS (ES$^+$) 444 (MH$^+$).

EXAMPLE 35

6,6-Dimethyl-9-methoxy-N-[2-(4-methylpiperazin-1-yl)pyridin-5-yl]-benzo[h]-5,6-dihydroquinazoline-2-amine From 2-chloro-6,6-dimethyl-9-methoxybenzo[h]-5,6-dihydroquinazoline (0.71 g, 2.60 mmol) and 5-amino-2-(4- methylpiperazin-1-yl)pyridine (0.5 g, 2.60 mmol) to give the title compound (200 mg) as a yellow solid m.p. 43°. δH (CDCl$_3$) 8.34 (1H, d, J 2.7 Hz), 8.19 (1H, s), 8.02 (1H, dd, J 9.0., 2.7 Hz), 7.85 (1H, d, J 2.9 Hz), 7.32 (1H, d, J 8.6 Hz), 7.00 (1H, dd, J 8.6, 2.9 Hz), 6.94 (1H, s), 6.70 (1H, d, J 9.0 Hz), 3.88 (3H, s), 3.55 (4H, m), 2.68 (2H, s), 2.59 (4H, m), 2.38 (3H, s) and 1.27 (6H, s). MS (ES$^+$) 431 (MH$^+$).

EXAMPLE 36

6,6-Dimethyl-9-methoxy-N-[2-(4-methylpiperazin-1-yl)-3-methylpyridin-5-yl]benzo[h]-5,6-dihydroquinazoline From 2-chloro-6,6-dimethyl-9-methoxybenzo[h]-5,6-dihydroquinazoline (600 mg, 2.18 mmol) and 5-amino-2-(4-methylpiperazin-1-yl)-3-methylpyridine (3450 mg, 2.18 mmol) to give the title compound (261 mg) as a pale yellow solid m.p., 187–188°. δH (CDCl$_3$) 8.29 (1H, d, J 2.5 Hz), 8.22 (1H, s), 8.07 (1H, s), 7.87 (1H, d, J 2.8 Hz), 7.33 (1H, d, J 8.6 Hz), 7.01 (2H, m), 3.90 (3H, s), 3.19 (4H, m), 2.67 (6H, m), 2.14 (3H, s), 2.33 (3H, s) and 1.28 (6H, s). MS (ES$^+$) 207 (MH$^+$).

Biological Activity

The following assays were used to demonstrate the activity and selectivity of compounds according to the invention. Enzymes for the assays were either obtained commercially or purified from known natural or recombinant sources using conventional methods.

p56$^{lck}$ kinase assay

The tyrosine kinase activity of p56$^{lck}$ was determined using a RR-src peptide (RRLIEDNEYTARG) and [γ-$^{33}$P] ATP as substrates. Quantitation of the $^{33}$P-phosphorylated peptide formed by the action of p56$^{lck}$ was achieved using an adaption of the method of Geissler et al (J. Biol. Chem. (1990) 265, 22255–22261).

All assays were performed in 20 mM HEPES pH 7.5 containing 10 mM MgCl$_2$, 10 mM MnCl$_2$, 0.05% Brij, 1 μM ATP (0.5μCi[γ-$^{33}$P]ATP) and 0.8 mg/ml RR-src. Inhibitors in dimethylsulphoxide (DMSO) were added such that the final concentration of DMSO did not exceed 1%, and enzyme such that the consumption of ATP was less than 10%. After incubation at 30° C. for 15min, the reaction was terminated by the addition of one-third volume of stop reagent (0.25 mM EDTA and 33 mM ATP in dH$_2$O). A 15 μl aliquot was removed, spotted onto a P-30 filtermat (Wallac, Milton Keynes, UK), and washed sequentially with 1% acetic acid and dH$_2$O to remove ATP. The bound $^{33}$P-RR-src was quantitated by scintillation counting of the filtermat in a Betaplate scintillation counter (Wallac, Milton Keynes, UK) after addition of Meltilex scintillant (Wallac, Milton Keynes, UK). The dpm obtained, being directly proportional to the amount of $^{33}$P-RR-src produced by p56$^{lck}$, were used to determine the IC$_{50}$ for each compound. The IC$_{50}$ was defined as the concentration of compound required to reduce the production of $^{33}$P-RR-src by 50%.

In this assay, compounds according to the invention have IC$_{50}$ values of around 100 nM or less.

p59$^{fyn}$ kinase assay

Compounds of the invention were assayed for p59$^{fyn}$ inhibitory activity in a similar manner to the p56$^{lck}$ assay using human p59$^{fyn}$.

The selectivity of compounds according to the invention can be determined in an assay utilising a serine/threonine kinase:

Protein kinase C assay

Inhibitor activity against protein kinase C (PKC) was determined using PKC obtained from Sigma Chemical Company (Poole, UK) and a commercially available assay system (Amersham International plc, Amersham, UK). Briefly, PKC catalyses the transfer of the γ-phosphate ($^{32}$p) of ATP to the threonine group on a peptide specific for PKC. Phosphonylated peptide is bound to phosphocellulose paper, subsequently quantified by scintillation counting, and IC$_{50}$ values determined as described above. In this assay compounds according to the invention have IC$_{50}$ values of 1 μM and above.

What is claimed is:

1. A compound of formula (1)

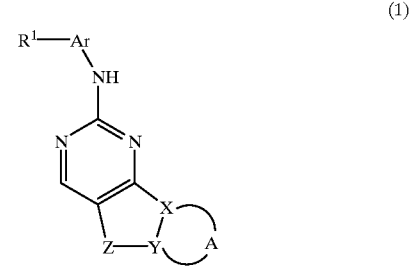

wherein

R$^1$ is a group —L$^1$R$^2$;

R$^2$ is a group —(Alk)$_m$L$^2$R$^3$;

Alk is an optionally substituted aliphatic or heteroaliphatic chains;

m is zero or the integer 1;

L$^1$ and L$^2$, which may be the same or different, are each a covalent bond or a linker atom or group selected from —O—, —S—, —C(O)—, —C(S)—, —S(O)—, —S(O)$_2$—, —N(R$^4$)—, —CON(R$^4$)—, —OC(O)N(R$^4$)—, —CSN(R$^4$)—, —N(R$^4$)CO—, —N(R$^4$)C(O)O—, —N(R$^4$)CS—, —SON(R$^4$), —SO$_2$N(R$^4$)—, —N(R$^4$)SO$_2$, —N(R$^4$)CON(R$^4$)—, —N(R$^4$)CSN(R$^4$)—, —N(R$^4$)SON(R$^4$)— and —N(R$^4$)SO$_2$N(R$^4$)—;

R$^3$ is an optionally substituted cycloaliphatic or heterocycloaliphatic group

Ar is an aryl or heteroaryl group;

X is a carbon atom;

Y is a carbon atom;

Z is a an optionally substituted C$_{1-2}$alkylene group;

A together with X and Y forms an optionally substituted phenyl group;

and the salts, solvates, hydrates and N-oxides thereof;

with the proviso that when m is zero L$^2$ is a covalent bond.

2. A compound according to claim 1 wherein Ar is an optionally substituted phenyl group.

3. A compound according to claim 1 wherein the linker group Z is an optionally substituted —(CH$_2$)$_2$— chain.

4. A compound according to claim 1 wherein R$^1$ is a group —L$^1$R$^2$ in which L$^1$ is a covalent bond or an oxygen atom and R$^2$ is a group —(Alk)$_m$R$^3$ in which Alk is an optionally substituted aliphatic or heteroaliphatic chain, m is zero or the integer 1 and R$^3$ is an optionally substitued cycloaliphatic or heterocycloaliphatic group.

5. A compound according to claim 4 wherein Alk is a C$_{1-6}$alkylene chain.

6. A compound according to claim 4 wherein R$^3$ is an optionally substituted C$_{3-7}$cycloalkyl group containing one or two heteroatoms.

7. A compound according to claim 4 wherein R$^3$ is an optionally substituted pyrrolidinyl, morpholinyl or piperazinyl group.

8. A compound which is:

6,6-Dimethyl-9-methoxy-N-[3-(2-pyrrolidinoethoxy)phenyl]benzo[h]-5,6-dihydroquinazoline-2-amine hydrochloride;

6,6-Dimethyl-9-methoxy-N-[4-(4-methylpiperazin-1-yl)phenyl]-benzo[h]-5,6-dihydroquinazoline-2-amine;

and the salts, solvates and hydrates thereof.

9. A pharmaceutical composition comprising a compound of formula

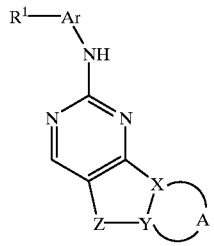

(1)

wherein $R^1$ is a group —$L^1R^2$;

$R^2$ is a group —(Alk)$_m L^2 R^3$;

Alk is an optionally substituted aliphatic or heteroaliphatic chain;

m is zero or the integer 1;

$L^1$ and $L^2$, which may be the same or different are each a covalent bond or a linker atom or group selected from —O—, —S—, —C(O)—, —C(S)—, —S(O)—, —S(O)2—, —N($R^4$)—, —CON($R^4$)—, —OC(O)N($R^4$)—, —CSN($R^4$)—, —N($R^4$)CO—, N($R^4$)C(O)O—, —N($R^4$)CS—, —SON($R^4$), —SO$_2$N($R^4$)—, —N($R^4$)SO$_2$—, —N($R^4$)CON($R^4$)—, —N($R^4$)CSN($R^4$)—, —N($R^4$)SON($R^4$)— and —N($R^4$)SO$_2$N($R^4$)—;

$R^3$ is an optionally substituted cycloaliphatic or heterocycloaliphatic group;

Ar is an aryl or heteroaryl group;

X is a carbon atom;

Y is a carbon atom;

Z is a an optionally substituted $C_{1-2}$alkylene group;

A together with X and Y forms an optionally substituted phenyl group;

and the salts, solvates, hydrates and N-oxides thereof;

with the proviso that when m is zero, $L^2$ is a covalent bond;

together with one or more pharmaceutically acceptable carriers, excipients or diluents.

* * * * *

UNITED STATES PATENT AND TRADEMARK OFFICE
CERTIFICATE OF CORRECTION

PATENT NO.    : 6,133,257
DATED         : October 17, 2000
INVENTOR(S)   : Batchelor et al.

It is certified that error appears in the above-identified patent and that said Letters Patent is hereby corrected as shown below:

Title page,
Item [56], OTHER PUBLICATIONS, "Kroon, A.P. et al." please delete "potassijm" and insert therefor -- potassium --;

Column 4,
Line 29, please delete "$C_{18}$" and insert therefor -- $C_{1-8}$ --;

Column 5,
Line 50, please delete "$N(R^11)SO_2$-,-$N(R^{11})SO_2N(R^{11})$-," and insert therefor -- $N(R^{10})SO_2$-,-$N(R^{10})SO_2N(R^{10})$-, --;

Column 8,
Line 26, please delete "benzoth]" and insert therefor -- benzo[h] --;

Column 9,
Line 51, please delete "long/kg" and insert therefor -- 10ng/kg --;

Column 14,
Line 11, please insert a -- - -- before "78º";

Column 17,
Line 45, please delete "benzofh]" and insert therefor -- benzo[h] --;

Column 18,
Line 64, please delete "benzofh]" and insert therefor -- benzo[h] --;

Column 19,
Line 56, please delete "6H" and insert therefor -- $\delta H$ --;
Line 63, please delete "methoxybenzofh]" and insert therefor -- methoxybenzo[h] --;

UNITED STATES PATENT AND TRADEMARK OFFICE
CERTIFICATE OF CORRECTION

PATENT NO.   : 6,133,257
DATED        : October 17, 2000
INVENTOR(S)  : Batchelor et al.

It is certified that error appears in the above-identified patent and that said Letters Patent is hereby corrected as shown below:

Column 23,
Line 22, please delete "169-1730 8H" and insert therefor -- 169-173°$\delta$H --;
Line 63, please delete "8H" and insert therefor -- $\delta$H --;

Column 24,
Line 47, please delete ""pyrrodin" and insert therefor -- pyrrolidin --;
Line 48, please delete "phenyllbenzo[h]" and insert therefor -- phenylbenzo[h] --;

Column 26,
Line 3, please delete "1H,brs" and insert therefor -- 1H, br s --;
Line 66, please delete " $^{3,4}$ - dimethoxy" and insert therefor -- 3,4-dimethoxy --;

Column 27,
Line 22, please delete "N-[$^{3,4}$ - dimethoxy" and therefor
-- N-3,4-dimethoxy --;
Line 31, please delete "8H" and insert therefor -- $\delta$H -- ;
Line 44, please delete "900" and insert therefor -- 90° --;

Column 30,
Line 60, please delete "(2H,brs)," and insert therefor -- (2H,br s), --;

Column 31,
Line 9, please delete "(1H,brs)"and insert therefor -- (1H, br s) --;

Column 34,
Line 27, please delete "chains" and insert therefor -- chain --;

UNITED STATES PATENT AND TRADEMARK OFFICE
CERTIFICATE OF CORRECTION

PATENT NO.    : 6,133,257
DATED         : October 17, 2000
INVENTOR(S)   : Batchelor et al.

It is certified that error appears in the above-identified patent and that said Letters Patent is hereby corrected as shown below:

Column 36,
Line 5, please delete "-S(O)2-," and insert therefor -- $-S(O)_2-$ --;

Signed and Sealed this

Twenty-eighth Day of January, 2003

JAMES E. ROGAN
*Director of the United States Patent and Trademark Office*